(12) United States Patent
Huang et al.

(10) Patent No.: US 8,728,985 B2
(45) Date of Patent: *May 20, 2014

(54) DISPLAY OF DISULFIDE LINKED DIMERIC PROTEINS IN FILAMENTOUS PHAGE

(75) Inventors: Chichi Huang, Radnor, PA (US); Tracy Spinka-Doms, Radnor, PA (US); Johan Fransson, San Diego, CA (US)

(73) Assignee: Centocor Ortho Biotech Inc., Horsham, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/509,292

(22) PCT Filed: Nov. 15, 2010

(86) PCT No.: PCT/US2010/056675
§ 371 (c)(1),
(2), (4) Date: May 11, 2012

(87) PCT Pub. No.: WO2011/062859
PCT Pub. Date: May 26, 2011

(65) Prior Publication Data
US 2012/0225085 A1 Sep. 6, 2012

Related U.S. Application Data

(60) Provisional application No. 61/261,767, filed on Nov. 17, 2009.

(51) Int. Cl.
*C40B 40/10* (2006.01)
(52) U.S. Cl.
USPC .......................................................... 506/18
(58) Field of Classification Search
None
See application file for complete search history.

(56) References Cited

U.S. PATENT DOCUMENTS

| | | | |
|---|---|---|---|
| 6,521,427 B1 | 2/2003 | Evans | |
| 6,670,127 B2 | 12/2003 | Evans et al. | |
| 6,753,136 B2 | 6/2004 | Park et al. | |
| 7,078,166 B2 | 7/2006 | Janda et al. | |
| 7,393,662 B2 | 7/2008 | Heavner et al. | |
| 2002/0103345 A1 | 8/2002 | Zhu | |
| 2003/0186322 A1* | 10/2003 | Janda et al. | 435/7.1 |
| 2005/0048617 A1 | 3/2005 | Wu et al. | |
| 2007/0148201 A1 | 6/2007 | Skerra et al. | |

FOREIGN PATENT DOCUMENTS

| | | |
|---|---|---|
| WO | WO 2004/002417 A2 | 1/2004 |
| WO | WO 2004/002424 A2 | 1/2004 |
| WO | WO 2005/005604 A2 | 1/2005 |
| WO | WO 2005/032460 A2 | 4/2005 |
| WO | WO 2005/081687 A2 | 9/2005 |
| WO | WO 2008/067547 A2 | 6/2008 |
| WO | WO 2009/085462 A1 | 7/2009 |

OTHER PUBLICATIONS

Gao, C. et al., "A method for the generation of combinatorial antibody libraries using pIX phage display", Proc Natl Acad Sci USA, vol. 99, pp. 12612-12616 (2002).

(Continued)

*Primary Examiner* — Christian Boesen
(74) *Attorney, Agent, or Firm* — Brian C. Carey

(57) ABSTRACT

Methods are provided for the display of a complex homodimer protein on the surface of a bacteriophage particle and combinatorial synthetic libraries of such proteins displayed as a fusion polypeptide with filamentous phage pIX coat protein. Heterodimeric or more complex interchain bonded structure, such as disulfide-linked, multimeric proteins, may be displayed using the method of the invention.

9 Claims, 14 Drawing Sheets

(56) References Cited

OTHER PUBLICATIONS

Shi, L. et al., "*De Novo* Selection of High-Affinity Antibodies from Synthetic Fab Libraries Displayed on Phage as pIX Fusion Proteins", Journal of Molecular Biology, vol. 397, pp. 385-396 (2010).

Tornetta, M. et al., "Antibody Fab display and selection through fusion to the pIX coat protein of filamentous phage", Journal of Immunological Methods, vol. 360, pp. 39-46 (2010).

Gao, C. et al., Making artificial antibodies: A format for phage display of combinatorial heterodimeric arrays, Proc Nat Acad Sci, vol. 96, pp. 6025-6030 (1999).

Kwasnikowski, et al., "Multivalent display system on filamentous bacteriophage pVll minor coat protein", Journal of Immunological Methods, vol. 307, p. 135 (2005).

Marks et al., By-passing Immunization, Journal of Molecular Biology, vol. 222, pp. 581-597 (1991).

Griffiths et al., "Isolation of high affinity human antibodies directly from large synthetic repertoires", J Embo, vol. 13, pp. 3245-3260 (1994).

Hoet et al., "Generation of high-affinity human antibodies by combining donor-derived and synthetic complementarity-determining region diversity", Nature Biotechnology, vol. 23, pp. 344-348 (2005).

Zwick eta I., "Homodimeric peptides displayed by the major coat protein of filamentous phage", Journal of Molecular Biology, vol. 300(2) pp. 307-320; Abstract (2000).

Lee et al., "Bivalent antibody phage display mimics natural immunoglobulin", Journal Immunological Methods, vol. 284 (1-2), pp. 119-132, Abstract, pp. 121 Fig 1 A,C (2004).

Mazor et al., "Selection of full-length IgGs by tandem display on filamentous phage particles and *Escherichia coli* fluorescence-activated cell sorting screening", The FEBS Journal, vol. 277, pp. 2291-2303, (2010).

International Search Report for PCT/US10/56675 dated Apr. 29, 2011.

Gao, C. et al., "A cell-penetrating peptide from a novel pVII-pIX phage-displayed random peptide library", Bioorganic & Medicinal Chemistry, Gergamon, GB, vol. 10 No. 12, pp. 4057-4065 (2002).

Kehoe, J. et al., "Filamentous phage display in the new Millenium", Chemical Reviews, American Chemical Society, US., vol. 105, No. 11 pp. 4056-4072 (2005).

European Search Report for EP 10 83 2033 dated Jun. 12, 2013 for Janssen Biotech, Inc.

* cited by examiner

*Fig. 2A-B*
A
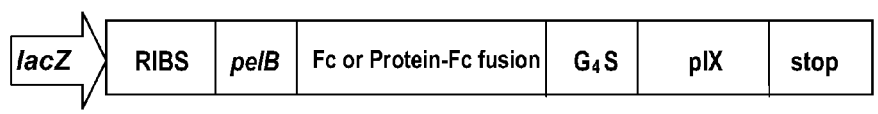
B
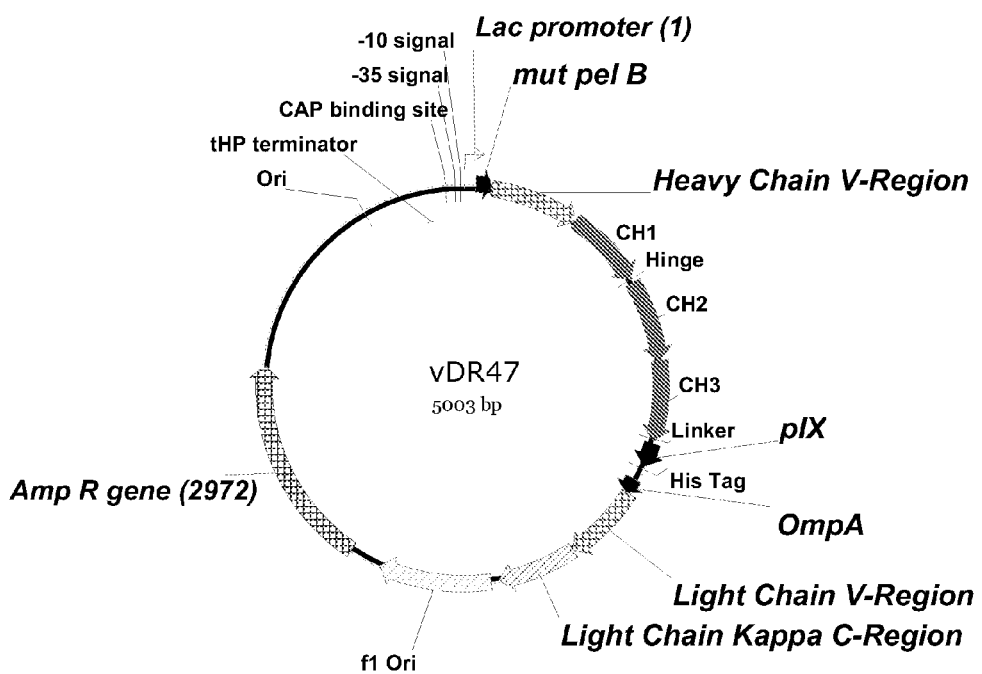

SEQUENCE LISTING

```
<160> NUMBER OF SEQ ID NOS: 26

<210> SEQ ID NO 1
<211> LENGTH: 15
<212> TYPE: PRT
<213> ORGANISM: Homo sapiens
<220> FEATURE:
<221> NAME/KEY: DOMAIN
<222> LOCATION: (11)..(15)
<223> OTHER INFORMATION: Hinge Core

<400> SEQUENCE: 1

Glu Pro Lys Ser Cys Asp Lys Thr His Thr Cys Pro Pro Cys Pro
1               5                   10                  15

<210> SEQ ID NO 2
<211> LENGTH: 12
<212> TYPE: PRT
<213> ORGANISM: Homo sapiens
<220> FEATURE:
<221> NAME/KEY: DOMAIN
<222> LOCATION: (4)..(12)
<223> OTHER INFORMATION: Hinge Core

<400> SEQUENCE: 2

Glu Arg Lys Cys Cys Val Glu Cys Pro Pro Cys Pro
1               5                   10

<210> SEQ ID NO 3
<211> LENGTH: 61
<212> TYPE: PRT
<213> ORGANISM: Homo sapiens
<220> FEATURE:
<221> NAME/KEY: DOMAIN
<222> LOCATION: (13)..(61)
<223> OTHER INFORMATION: Hinge Core

<400> SEQUENCE: 3

Glu Leu Lys Thr Pro Leu Gly Asp Thr Thr His Thr Cys Pro Arg Cys
1               5                   10                  15

Pro Glu Lys Ser Cys Asp Thr Pro Pro Pro Cys Pro Arg Cys Pro Glu
                20                  25                  30

Pro Lys Ser Cys Asp Thr Pro Pro Pro Cys Pro Arg Cys Pro Cys Pro
            35                  40                  45

Lys Ser Cys Asp Thr Pro Pro Pro Cys Pro Arg Cys Pro
        50                  55                  60

<210> SEQ ID NO 4
<211> LENGTH: 12
<212> TYPE: PRT
<213> ORGANISM: Homo sapiens
<220> FEATURE:
<221> NAME/KEY: DOMAIN
<222> LOCATION: (8)..(12)
<223> OTHER INFORMATION: Hinge Core

<400> SEQUENCE: 4
```

```
Glu Ser Lys Tyr Gly Pro Pro Cys Pro Ser Cys Pro
1               5                   10
```

<210> SEQ ID NO 5
<211> LENGTH: 110
<212> TYPE: PRT
<213> ORGANISM: Homo sapiens

<400> SEQUENCE: 5

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110
```

<210> SEQ ID NO 6
<211> LENGTH: 109
<212> TYPE: PRT
<213> ORGANISM: Homo sapiens

<400> SEQUENCE: 6

```
Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser His Glu Asp Pro Glu Val Gln Phe Asn Trp Tyr Val
            35                  40                  45

Asp Gly Val Glu Val His Asn Ala Lys Thr Lys Pro Arg Glu Glu Gln
        50                  55                  60

Phe Asn Ser Thr Phe Arg Val Val Ser Val Leu Thr Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys
            100                 105
```

<210> SEQ ID NO 7
<211> LENGTH: 110
<212> TYPE: PRT
<213> ORGANISM: Homo sapiens

<400> SEQUENCE: 7

```
Ala Pro Glu Leu Leu Gly Gly Pro Ser Val Phe Leu Pro Pro Lys
1               5                   10                  15

Pro Lys Asp Thr Leu Met Ile Ser Arg Thr Pro Glu Val Thr Cys Val
                20                  25                  30

Val Val Asp Val Ser His Glu Asp Pro Glu Val Gln Phe Lys Trp Tyr
            35                  40                  45

Val Asp Gly Val Glu Val His Asn Ala Lys Thr Lys Pro Arg Glu Glu
        50                  55                  60
```

```
Gln Tyr Asn Ser Thr Phe Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Thr Lys
            100                 105                 110
```

<210> SEQ ID NO 8
<211> LENGTH: 110
<212> TYPE: PRT
<213> ORGANISM: Homo sapiens

<400> SEQUENCE: 8

```
Ala Pro Glu Phe Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
                 20                  25                  30

Val Val Asp Val Ser Gln Glu Asp Pro Glu Val Gln Phe Asn Trp Tyr
             35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Gly Leu Pro Ser Ser Ile Glu Lys Thr Ile Ser Lys Ala Lys
            100                 105                 110
```

<210> SEQ ID NO 9
<211> LENGTH: 107
<212> TYPE: PRT
<213> ORGANISM: Homo sapiens

<400> SEQUENCE: 9

```
Gly Gln Pro Arg Glu Pro Gln Val Tyr Thr Leu Pro Pro Ser Arg Asp
 1               5                  10                  15

Glu Leu Thr Lys Asn Gln Val Ser Leu Thr Cys Leu Val Lys Gly Phe
                 20                  25                  30

Tyr Pro Ser Asp Ile Ala Val Glu Trp Glu Ser Asn Gly Gln Pro Glu
             35                  40                  45

Asn Asn Tyr Lys Thr Thr Pro Pro Val Leu Asp Ser Asp Gly Ser Phe
 50                  55                  60

Phe Leu Tyr Ser Lys Leu Thr Val Asp Lys Ser Arg Trp Gln Gln Gly
 65                  70                  75                  80

Asn Val Phe Ser Cys Ser Val Met His Glu Ala Leu His Asn His Tyr
                 85                  90                  95

Thr Gln Lys Ser Leu Ser Leu Ser Pro Gly Lys
            100                 105
```

<210> SEQ ID NO 10
<211> LENGTH: 107
<212> TYPE: PRT
<213> ORGANISM: Homo sapiens

<400> SEQUENCE: 10

```
Gly Gln Pro Arg Glu Pro Gln Val Tyr Thr Leu Pro Pro Ser Arg Glu
 1               5                  10                  15

Glu Met Thr Lys Asn Gln Val Ser Leu Thr Cys Leu Val Lys Gly Phe
```

```
                    20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Met Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 11
<211> LENGTH: 107
<212> TYPE: PRT
<213> ORGANISM: Homo sapiens

<400> SEQUENCE: 11

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Ser Gly Gln Pro Glu
            35                  40                  45

Asn Asn Tyr Asn Thr Thr Pro Pro Met Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Ile Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 12
<211> LENGTH: 107
<212> TYPE: PRT
<213> ORGANISM: Homo sapiens

<400> SEQUENCE: 12

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 13
<211> LENGTH: 8
<212> TYPE: PRT
<213> ORGANISM: Homo sapiens
```

```
<400> SEQUENCE: 13

Gly Thr Leu Val Thr Val Ser Ser
1               5

<210> SEQ ID NO 14
<211> LENGTH: 22
<212> TYPE: PRT
<213> ORGANISM: Erwinia carotovora
<220> FEATURE:
<221> NAME/KEY: MUTAGEN
<222> LOCATION: (6)..(6)
<223> OTHER INFORMATION: X may be P or S

<400> SEQUENCE: 14

Met Lys Tyr Leu Leu Xaa Thr Ala Ala Ala Gly Leu Leu Leu Leu Ala
1               5                   10                  15

Ala Gln Pro Ala Met Ala
            20

<210> SEQ ID NO 15
<211> LENGTH: 21
<212> TYPE: PRT
<213> ORGANISM: Escherichia coli
<220> FEATURE:
<221> NAME/KEY: MUTAGEN
<222> LOCATION: (11)..(11)
<223> OTHER INFORMATION: X may be A or P

<400> SEQUENCE: 15

Met Lys Lys Thr Ala Ile Ala Ile Ala Val Xaa Leu Ala Gly Phe Ala
1               5                   10                  15

Thr Val Ala Gln Ala
            20

<210> SEQ ID NO 16
<211> LENGTH: 20
<212> TYPE: PRT
<213> ORGANISM: Artificial sequence
<220> FEATURE:
<223> OTHER INFORMATION: A fusion protein comprising a synthetic
      bioactive erythropoieticpeptide (EMP-1), synthetic linker, and
      human IgG sequences.

<400> SEQUENCE: 16

Gly Gly Thr Tyr Ser Cys His Phe Gly Pro Leu Thr Trp Val Cys Lys
1               5                   10                  15

Pro Gln Gly Gly
            20

<210> SEQ ID NO 17
<211> LENGTH: 224
<212> TYPE: PRT
<213> ORGANISM: Homo sapiens

<400> SEQUENCE: 17

Gly Ser Cys Pro Pro Cys Pro Ala Pro Glu Ala Ala Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser Gln Glu Asp Pro
        35                  40                  45

Glu Val Gln Phe Asn Trp Tyr Val Asp Gly Val Glu Val His Asn Ala
    50                  55                  60
```

-continued

```
Lys Thr Lys Pro Arg Glu Glu Gln Phe Asn Ser Thr Tyr Arg Val Val
 65                  70                  75                  80

Ser Val Leu Thr Val Leu His Gln Asp Trp Leu Asn Gly Lys Glu Tyr
                 85                  90                  95

Lys Cys Lys Val Ser Asn Lys Gly Leu Pro Ser Ser Ile Glu Lys Thr
            100                 105                 110

Ile Ser Lys Ala Lys Gly Gln Pro Arg Glu Pro Gln Val Tyr Thr Leu
        115                 120                 125

Pro Pro Ser Gln Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Arg Leu Thr Val Asp Lys Ser
            180                 185                 190

Arg Trp Gln Glu Gly Asn Val Phe Ser Cys Ser Val Met His Glu Ala
        195                 200                 205

Leu His Asn His Tyr Thr Gln Lys Ser Leu Ser Leu Ser Leu Gly Lys
    210                 215                 220
```

<210> SEQ ID NO 18
<211> LENGTH: 242
<212> TYPE: PRT
<213> ORGANISM: Homo sapiens

<400> SEQUENCE: 18

```
Gly Gly Gly Gly Ser Gly Thr Leu Val Thr Val Ser Ser Glu Ser Lys
  1               5                  10                  15

Tyr Gly Pro Pro Cys Pro Pro Cys Pro Ala Pro Glu Ala Ala Gly Gly
             20                  25                  30

Pro Ser Val Phe Leu Phe Pro Pro Lys Pro Lys Asp Thr Leu Met Ile
         35                  40                  45

Ser Arg Thr Pro Glu Val Thr Cys Val Val Val Asp Val Ser Gln Glu
 50                  55                  60

Asp Pro Glu Val Gln Phe Asn Trp Tyr Val Asp Gly Val Glu Val His
 65                  70                  75                  80

Asn Ala Lys Thr Lys Pro Arg Glu Glu Gln Phe Asn Ser Thr Tyr Arg
                 85                  90                  95

Val Val Ser Val Leu Thr Val Leu His Gln Asp Trp Leu Asn Gly Lys
            100                 105                 110

Glu Tyr Lys Cys Lys Val Ser Asn Lys Gly Leu Pro Ser Ser Ile Glu
        115                 120                 125

Lys Thr Ile Ser Lys Ala Lys Gly Gln Pro Arg Glu Pro Gln Val Tyr
130                 135                 140

Thr Leu Pro Pro Ser Gln Glu Glu Met Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Arg Leu Thr Val Asp
        195                 200                 205

Lys Ser Arg Trp Gln Glu Gly Asn Val Phe Ser Cys Ser Val Met His
    210                 215                 220
```

```
Glu Ala Leu His Asn His Tyr Thr Gln Lys Ser Leu Ser Leu Ser Leu
225                 230                 235                 240

Gly Lys

<210> SEQ ID NO 19
<211> LENGTH: 98
<212> TYPE: PRT
<213> ORGANISM: Homo sapiens

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 20
<211> LENGTH: 232
<212> TYPE: PRT
<213> ORGANISM: Homo sapiens

<400> SEQUENCE: 20

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

```
Ser Cys Ser Val Met His Glu Ala Leu His Asn His Tyr Thr Gln Lys
    210                 215                 220
Ser Leu Ser Leu Ser Pro Gly Lys
225                 230
```

<210> SEQ ID NO 21
<211> LENGTH: 4
<212> TYPE: PRT
<213> ORGANISM: Artificial Sequence
<220> FEATURE:
<223> OTHER INFORMATION: A fusion protein comprising a synthetic a
      filamentous phage particle, the fusion between the exogenous
      polypeptide and the filamentous phage pVII or pIX protein

<400> SEQUENCE: 21

Gly Gly Gly Ser
1

<210> SEQ ID NO 22
<211> LENGTH: 4
<212> TYPE: PRT
<213> ORGANISM: Artificial Sequence
<220> FEATURE:
<223> OTHER INFORMATION: A fusion protein comprising a synthetic a
      filamentous phage particle, the fusion between the exogenous
      polypeptide and the filamentous phage pVII or pIX protein

<400> SEQUENCE: 22

Gly Gly Gly Ser
1

<210> SEQ ID NO 23
<211> LENGTH: 4
<212> TYPE: PRT
<213> ORGANISM: Artificial Sequence
<220> FEATURE:
<223> OTHER INFORMATION: Synthetic sequence comprising a linker fusion
      protein

<400> SEQUENCE: 23

Gly Gly Ser Gly
1

<210> SEQ ID NO 24
<211> LENGTH: 4
<212> TYPE: PRT
<213> ORGANISM: Artificial Sequence
<220> FEATURE:
<223> OTHER INFORMATION: Synthetic sequence comprising an IgG1 type
      hinge

<400> SEQUENCE: 24

Cys Pro Pro Cys
1

<210> SEQ ID NO 25
<211> LENGTH: 13
<212> TYPE: PRT
<213> ORGANISM: Artificial Sequence
<220> FEATURE:
<223> OTHER INFORMATION: Synthetic sequence comprising a mutant IgG4
      with hinge core
<220> FEATURE:
<221> NAME/KEY: UNSURE
<222> LOCATION: (1)..(2)
<223> OTHER INFORMATION: Wherein Xaa can be any naturally occurring
      amino acid
<220> FEATURE:
<221> NAME/KEY: UNSURE
<222> LOCATION: (4)..(10)

```
<223> OTHER INFORMATION: Wherein Xaa can be any naturally occurring
      amino acid
<220> FEATURE:
<221> NAME/KEY: UNSURE
<222> LOCATION: (12)..(13)
<223> OTHER INFORMATION: Wherein Xaa can be any naturally occurring
      amino acid

<400> SEQUENCE: 25

Xaa Xaa Cys Xaa Xaa Xaa Xaa Xaa Xaa Xaa Cys Xaa Xaa
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic sequence comprising mutant IgG4 with
      V-region and full hinge
<220> FEATURE:
<221> NAME/KEY: UNSURE
<222> LOCATION: (1)..(2)
<223> OTHER INFORMATION: Wherein Xaa can be any naturally occurring
      amino acid
<220> FEATURE:
<221> NAME/KEY: UNSURE
<222> LOCATION: (4)..(11)
<223> OTHER INFORMATION: Wherein Xaa can be any naturally occurring
      amino acid
<220> FEATURE:
<221> NAME/KEY: UNSURE
<222> LOCATION: (13)..(14)
<223> OTHER INFORMATION: Wherein Xaa can be any naturally occurring
      amino acid

<400> SEQUENCE: 26

Xaa Xaa Cys Xaa Xaa Xaa Xaa Xaa Xaa Xaa Xaa Cys Xaa Xaa
1               5                   10
```

DISPLAY OF DISULFIDE LINKED DIMERIC PROTEINS IN FILAMENTOUS PHAGE

CROSS-REFERENCE TO RELATED APPLICATIONS

This application claims the benefit of International Application Number PCT/US2010/056675, filed 15 Nov. 2010, which claims the benefit of U.S. Provisional Application No. 61/261,767, filed 17 Nov. 2009. The entire contents of each of the aforesaid applications are incorporated herein by reference in their entirety.

BACKGROUND

1. Field of the Invention

The invention relates to compositions and methods for generating and using pIX phage display libraries for producing dimeric antibody fragments, whole antibodies, or other disulfide linked multimeric constructs.

2. Discussion of the Field

Filamentous phage display is a widely used technology for affinity-based selection of proteins as each phage particle links the nucleic acid encoding the polypeptide fused to the N-terminus of its coat protein together in the selection process. M13 bacteriophage encodes five coat proteins with approximately five copies of the minor coat proteins pIII and pVI at one end of the phage and the same number of pVII and pIX at other end of the phage. The phage DNA is encapsulated by approximately 3000 copies of the major coat protein, pVIII. Although the display of foreign polypeptides has been accomplished with each of the coat proteins of M13, pIII and pVIII are by far the most common fusion partners. Using this technique, libraries of peptides, Fabs, scFvs and other protein binders have been constructed and found use in diverse applications and with great commercial value.

The pIII coat protein has been favored over the pVIII protein due to its size, conformation and low copy number. The pIII minor coat protein is a 404 amino acid, 42 kD protein responsible for phage infection into *E. coli* comprising three domains connected by flexible hinge segments. Fusions to the pIII N-terminus tether the displayed protein away from the phage surface, providing potentially greater access for ligand binding than for fusion to the small, high copy number pVIII coat protein. The pIII protein is essential for the initial steps of infection and fusions of all but small peptides and proteins can interfere with this process. This issue is circumvented for example by the use of virus vectors containing a second copy of a wild-type pIII protein or phagemid systems that employ helper phage. In contrast to pIII and like pVIII, pVII and pIX are short helical proteins of 33 and 32 aa, respectively, closely packed on the phage surface. Nevertheless, scFv (Gao, C. et al. Proc Natl Acad Sci USA 99, 12612-12616, 2002) and Fab (Shi, L et al. J Mol Biol 397, 385-396, 2010; Tornetta, M et al. J Immunol Meth 360, 39-46, 2010) libraries have been displayed and selected on pIX. Heterodimeric display of Fv and peptides has been described by fusing different polypeptides to both pVII and the closely adjacent pIX (Gao, et al. 1999 Proc Nat Acad Sci 96: 6025-6030 and Janda U.S. Pat. No. 7,078,166). In addition, pVII display of monospecific scFv has been reported (Kwasnikowski, et al. 2005. J Immunol Methods 307:135). An alternative approach in which exoproteins encoded by the phage or phagemid vector are not fused to the coat protein but rather covalently attach to re-engineered coat proteins pIII and pIX with through disulfide bonding has also been described (U.S. Pat. No. 6,753,136).

The ability to display a dimeric protein on the surface of a phage particle as well as a heterodimeric protein is advantageous in mimicking more complex protein structures in a combinatorial library format. There is a continuing need to advance the art for generating high throughput methods of screening variants of complex proteins such as that of the human IgG, which is a homodimer of heavy and light chain pairs (heterodimers) connected via intermolecular disulfide bonds. To date, it has not been possible to demonstrate the correct assembly and display of complete antibody heavy chains on filamentous phage. The libraries and methods of this invention meet these needs by coupling comprehensive design, assembly technologies, and phage pIX Fab display.

SUMMARY OF THE INVENTION

The present invention provides a facile means for display of dimeric, disulfide linked proteins and more complex structures on filamentous phage using the M13 coat protein, pIX. In the present invention the protein displayed is a fusion protein comprising a pIX coat protein, a folded-domain, such as a CH2-domain, linked to a mulitmerizing domain comprising cysteine residues, such as hinge domain. In a specific embodiment the dimeric protein, is a homodimer wherein the members are disulfide linked and the protein comprises an antibody Fc. In another embodiment, the homodimeric, disulfide linked protein comprises a human antibody protein, wherein at least the hinge domain and a constant domain are present in each of the polypeptides comprising the homodimer and, optionally, the homodimeric structure further associates with independently expressed antibody light chains by disulfide bond formation.

The invention provides a replicable vector coding for at least one fusion protein, having a sequence encoding an exogenous polypeptide fused to a sequence encoding the pIX coat protein, wherein the exogenous non-phage protein portion is homodimer-forming polypeptide chain. In one embodiment, the fused homo-dimer-forming polypeptide forms an Fc-fusion protein. In another embodiment, the homodimeric structure may further associate with a heteropolypeptide to form a more complex structure. In one aspect, the display of both an antibody heavy chain polypeptide and a light chain polypeptide in a single phage molecule results in the assembly of a functional antibody molecule at the surface of the phage particle, such as, but not limited to a complete IgG molecule. Included in the invention are host cells containing the replicable vector and a phage particle which is capable of displaying the fusion polypeptide on the surface of the phage as a dimeric disulfide-linked protein. The vector, optionally, comprises a polynucleotides encoding a secretion signal operably fused to the polynucleotide sequences encoding the displayed polypeptide-coat protein fusion.

Also provided, are methods and vectors for constructing a pIX phage display de novo library of dimeric disulfide-linked proteins useful for assembly, screening and such other interrogative techniques as are practiced in the art, for selection and improvement of antibody compositions. In a one embodiment, libraries of host cells containing phage particles displaying a plurality of different fusion polypeptides which are capable of forming multimeric structures on the phage particle surface linked to a pIX protein. In one aspect, the library is encoded in a phagemid system.

In one embodiment, a library of the invention may comprise a library of heavy chain variable regions; it may further comprise a library of light chain variable regions; and it may further comprise a library of variant Fc regions. A library of the invention may be subjected to panning, sorting, or other selection procedures in order to identify and isolated polynucleotides from the library encoding proteins having a desired, enhanced, or diminished property such as altered binding to a target ligand or having an altered binding for effector molecules (e.g., FcγRs and/or C1q).

BRIEF DESCRIPTION OF THE SEVERAL VIEWS OF THE DRAWING

FIG. 2 A-B Schematics of the pIX phagemid vector for a Fc-forming construct (A) showing the relative positions of the lacZ promoter; the ribosomal binding site (RIBS), which was added upstream of the bacterial signal peptide, pelB; the position of the flexible linker ($G_4S$), connecting the polynucleotide sequence encoding the Fc polypeptide, and phage minor coat protein pIX or pVII; and the dicistronic phagemid vector (B) for expression of full IgG structures on pIX.

BRIEF DESCRIPTION OF THE SEQUENCE LISTING

Figure 1:
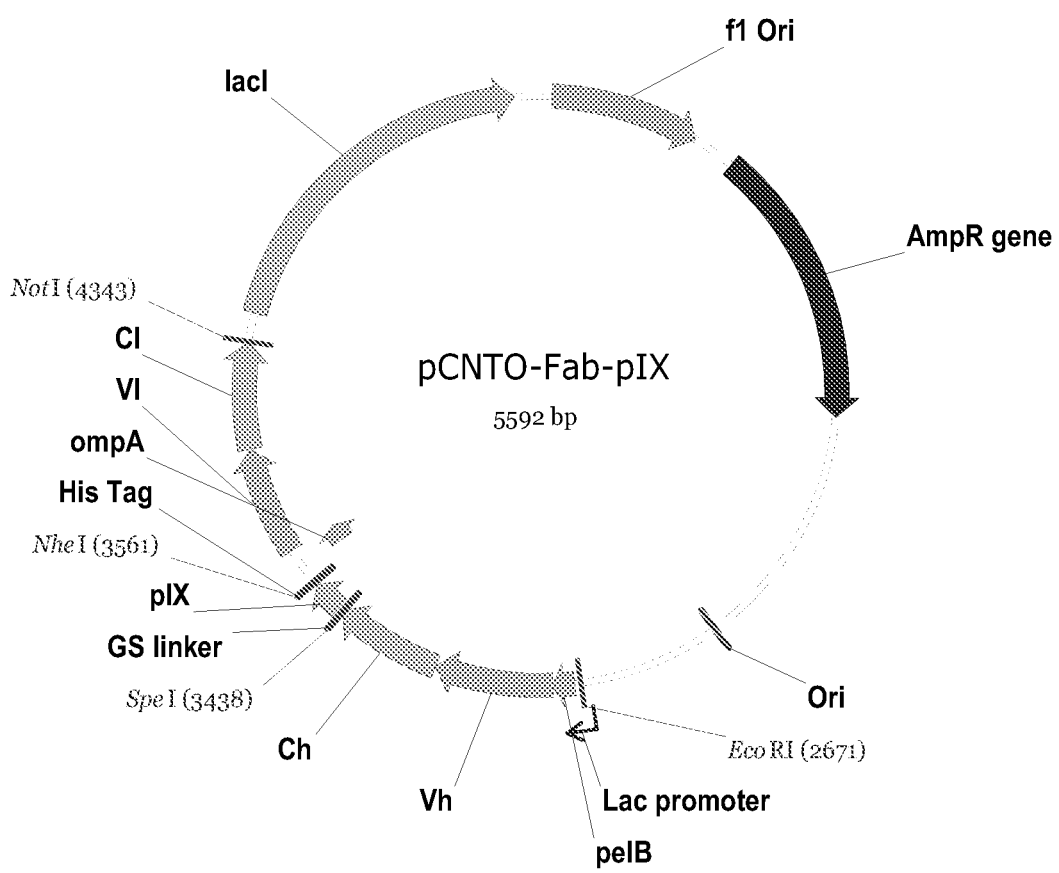
FIG. 1. Diagram of the starting vector used to express a pIX-tethered Fab.

| SEQ ID NO: | Description | Features |
|---|---|---|
| 1 | IgG1 hinge | core 11-15 |
| 2 | IgG2 hinge | core 8-12 |
| 3 | IgG3 hinge | Core 13-61 |
| 4 | IgG4 hinge | Core 8-12 |
| 5 | IgG1 CH2 | |
| 6 | IgG2 CH2 | |
| 7 | IgG3 CH2 | |
| 8 | IgG4 CH2 | |
| 9 | IgG1 CH3 | |
| 10 | IgG2 CH3 | |
| 11 | IgG3 CH3 | |
| 12 | IgG4 CH3 | |
| 13 | J-piece | |
| 14 | pel B | P6S |
| 15 | ompA | A11P |
| 16 | EMP-1 | |
| 17 | Mutant IgG4 Fc forming type 1 polypeptide | |
| 18 | Mutant IgG4 Fc forming type 2 polypeptide | |
| 19 | human IgG1 CH1 domain | |
| 20 | human IgG1 Fc-forming protein | |
| 21 | Synthetic Sequence | |
| 22 | Synthetic Sequence | |
| 23 | Synthetic Sequence | |
| 24 | Synthetic Sequence | |
| 26 | Synthetic Sequence | |

DETAILED DESCRIPTION OF THE INVENTION

Abbreviations

ADCC=antibody-dependent cell-mediated cytotoxicity, ADMC=antibody-dependent monocyte-mediated cytotoxicity, c1q=complement factor 1q, EPO=recombinant erythropoietin, FcR=Fc receptor; Ig=immunoglobulin; Hc=heavy chain; Lc=light chain; IPTG=isopropylthio-β-galactoside;

Definitions

As used herein, unless otherwise indicated or clear from the context, antibody domains, regions and fragments are accorded standard definitions as are well known in the art. The proteins of the invention are derived from, or incorporate portions of antibodies of one or more immunoglobulin classes Immunoglobulin classes include IgG, IgM, IgA, IgD, and IgE isotypes and, in the case of IgG and IgA, their subtypes, e.g. $IgG_1$, $IgG_2$, $IgG_3$, and $IgG_4$.

By "cistron" is meant a sequence of nucleotides in a DNA molecule coding for an amino acid sequence and including upstream and downstream DNA expression control elements.

By "exogenous polypeptide" or "exogenous protein" or "exoprotein" is meant a protein not normally encoded by the wild-type filamentous phage genome, but rather is foreign to the normal phage protein. A typical exogenous polypeptide is any polypeptide of interest, including an antibody immunoglobulin heavy chain (Hc) domain or immunoglobulin light chain (Lc) domain, an immunoglobulin heavy chain variable domain ($V_H$), an immunoglobulin light chain variable domain ($V_L$), natural or synthetic polypeptides, a single chain antibody (scFv), or a sequence or combination of immunoglobulin domains such as they occur in nature especially as an Fc domain which may include CH3, CH2, a hinge region and/or a CH1 domain or fragment thereof.

By "Fc", a label given the crystallizable cleavage fragment of a papain digested IgG; is meant a functional fragment of an antibody comprising a dimeric structure of polypeptide chains derived from antibody constant domains and having interchain linkages of disulfide bonds. In human IgG1, papain creates a fragment C-terminal to Cys226 (numbered using the EU index as in Kabat et al., *Sequences of Proteins of Immunological Interest*, 5th Ed. Public Health Service, National Institutes of Health, Bethesda, Md. (1991), which is expressly incorporated herein by reference. The "EU index as in Kabat" refers to the residue numbering of the human IgG1 EU antibody. Although the definition of N-terminal residue of the Fc may vary, it is generally appreciated to include at least residue 223 in the Kabat numbering system, which is the third residue N-terminal to the first interchain bonding cysteine (C226 in the Kabat system). The Fc portion of the molecule is not directly involved in contact of the antibody with its specific target antigen, but mediates effector functions. These functions are of two types: (1) functions that require binding of the antibody to an antigen, such as C1q binding and/or complement dependent cytotoxicity (CDC) activity or ADCC and ADMC following Fc-receptor gamma-type binding for IgG, Fc-receptor epsilon binding for IgE, and Fc-receptor alpha binding for IgA; and (2) functions that are independent of antigen binding such as persistence in the circulation by the ability to bind FcRn and be transcytosed across cellular and tissue barriers (such as the gut). The ability to significantly increase the serum half-life of antibody molecules or other molecules via the fusion of an Fc, in particular, is highly advantageous. Longer lived molecules may reduce the amount needed in clinical treatments, thereby reducing and frequency of administration.

The terms "Fc receptor" or "FcR" are used to describe a receptor that binds to the Fc region of an antibody. FcR include FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof Activating receptor FcγRIIA contains an immunoreceptor tyrosine-based activation motif (FAM) in its cytoplasmic domain. Inhibiting receptor FcγRIIB contains an immunoreceptor tyrosine-based inhibition motif (ITIM) in its cytoplasmic domain (see review in Daëron, Annu. Rev. Immunol., 1997, 15:203-234; FcRs are reviewed in Ravetch and Kinet, Annu. Rev. Immunol., 1991, 9:457-92; Capel et al., Immunomethods, 1994, 4:25-34; and de Haas et al., J. Lab. Clin. Med., 1995, 126:330-41, each of which is incorporated herein by reference).

By "fusion polypeptide" or "fusion protein" is meant a fusion polypeptide (protein) comprising first and second polypeptides encoded by first and second nucleic acid sequences, respectively, which are operatively linked. As used herein, it is understood that a fusion protein contains components and domains that are "operatively linked" meaning that the fused elements of a polypeptide or polynucleotide, for example, are linked such that each performs or functions as intended. For example, an element that regulates expression, such as a promoter, operator, or enhancer, can be operatively linked to the nucleotide sequence whose expression is to be regulated. Linkage between and among elements may be direct or indirect, such as via a linker. The elements are not necessarily adjacent.

The term "library" denotes a collection of encoded proteins which are variants, that is, where certain regions are the same or similar and other regions vary. The variation regions may be by directed or random variation (stochastic or nonstochastic changes). A library or variants can be described in terms of number of different variants or "size" of the library. A useful de novo antibody library has high diversity ($>10^{10}$), amenable to alteration, easy to assemble, and have a low background of undesired sequences. Coupling the following methods accelerates library assembly and leads to low background: (a) Kunkel-based single-stranded mutagenesis; (b) palindromic loop with restriction site and; (c) use of a megaprimer approach.

A "phagemid" or "phage vector" is a cloning and expression vector that contains components derived from both phage chromosomes and exogenous DNA such as that from plasmids. As the phagemid contains a portion of a phage genome, upon co-infection of the host with a helper phage, it can be packaged into phage particles. A phagemid of the invention can be packaged into phage M13 particles. The phagemid or phage vector has been manipulated by insertion or incorporation of heterologous DNA, such as nucleic acid encoding the fusion proteins herein or expression cassettes provided herein. Such expression vectors typically contain a promoter sequence for efficient transcription of the inserted nucleic acid in the host cell.

Overview

Natural antibodies, which are bivalent antigen binding proteins, rely on Fc constant domains and hinge regions for proper association of the heavy chains. The CH2- and CH3 domains are preferably derived from human germline sequences such as those disclosed in WO2005005604 or that can be found by searching databases comprising the sequences of natural or engineered antibody sequences. In general, the protein constructs of the invention comprise a hinge region linked to one or more constant domains or portions thereof. It is usually desired to incorporate all constant domains normally present in an Fc: a hinge as shown in SEQ ID NO: 1-4 or portion thereof containing one or more cysteine residues or other sulfide or selenosulfide bond forming residue; a $CH_2$ as exemplified by SEQ ID NO: 5-8 or variants thereof, and $CH_3$ as exemplified by SEQ ID NO: 9-12 or variants thereof, in order to retain all the associated functions such as the ability bind receptors and increase persistence in the body. It will be appreciated by those in the art, that the sequences represented by those provided herein are nonlimiting and natural and variant antibody domains sequences can be found in various databases on the internet or in numerous publications which can be useful in the practice of the present invention. In addition, the constructs may, optionally, comprise some or all of a CH1 domain or some or all of an antibody variable domain may also be present such as that of SEQ ID NO: 13. These domains will, of course, will be present in a full IgG construct. Other antibody sequences and non-antibody sequences may be included as necessary for proper expression and folding of the antibody domains, such as signal peptides or secretion peptides such as those of encoding the amino acid sequence of SEQ ID NO: 14 (pelB) and 15 (ompA). However, the invention contemplates structures inclusive of only certain constant domains and not others, as well as structures where nonantibody derived domains may be present.

As various Fc functions depend on different portions of the Fc, fewer $C_H$ domains can be incorporated in the heavy chain if less than full functionality is desired. For example, significant activation of complement requires $CH_2$ of IgG or $CH_3$ of IgM. The invention also contemplates the use of modified hinge and Fc heavy chain domains which may have amino acids substituted, deleted, inserted or modified, so long as the heavy chains can associate in a stable complex.

In addition, the dimeric covalently linked structure which will typically form as a disulfide linked structure could also be formed by selenocysteine bonding, homocysteine bonding, or mixed sulphide-selenide bonding. In addition to the antibody hinge comprising the interchain covalent bonding residues, other multimerizing domains may be substituted to form dimeric or higher order structures. These mulitmerizing domains may be natural or artificial, such as a single cysteine or selenocysteine residue or include a motif, such as a leucine zipper motif, to assist in the association of the polypeptides of the exoprotein-coat protein fusion proteins on the surface of the phage particle.

In the case of full antibody proteins, the heavy chain-light chain heterodimers associate via particular heavy chain constant domains, to form structures of higher order. For example, IgG type antibodies comprise two heavy chain—light chain heterodimers joined by covalent linkage in a tetrameric structure. Certain other antibody types comprise similar tetrameric structures which are incorporated into a higher order structure comprising, for example, two tetramers (IgA) or ten tetramers (IgM).

In using phage coat proteins to display large exoprotein molecules, the protein displayed may interfere with assembly of recombinant phage particles if linked to all copies of the coat protein. In order to avoid assembly interference, a phagemid system, such as described by (Gao et al., *Proc Natl Acad Sci USA*, 99:12612-12616, 2002) for pIX display, may be used whereby both wild-type and exoprotein-linked coding sequences are present in the vector and both proteins are incorporated into the recombinant phage particle.

The applicants of the present invention have unexpectedly found that the antibody components forming the Fc portion of an antibody as described herein may be displayed as a fusion protein to pIX or pVII coat protein on the surface of a filamentous phage particle as a homodimeric disulfide linked protein displaying known biologic activities of the Fc-domain of a natural antibody, such as Fc-receptor binding, and, when in the form of a bivalent antigen-binding protein, capable of antigen binding. Thus, in contrast to monomeric, monovalent display of antibody binding fragments on phage particles, multimeric display of multivalent protein display is contemplated. Thus, the present invention provides a system of for manipulation and selection among a more complete spectrum of functional characteristics of natural antibodies. Such characteristics include those Fc functions which promote immune responses directed against cells displaying a particular antigen of interest on the cell surface, and which are important components of the biological activity of a manufactured antibody-like therapeutics Immune system effector cells include antigen specific cells such as T cells which activate cellular immune responses and nonspecific cells such as macrophages, neutrophils and natural killer (NK) cells which mediate cellular immune responses.

Method of Making the Invention

In the fusion protein displayed on a filamentous phage particle, the "fusion" between the exogenous polypeptide and the filamentous phage pVII or pIX protein may be directly linked by an amide linkage, or may comprise a linker polypeptide (i.e., a "linker"). Any of a variety of linkers may be used which are typically a stretch of about 5 to 50 amino acids in length. Particularly preferred linkers provide a high degree of mobility to the fusion protein at the point of the linker. Linkers devoid of secondary structure such as those comprised of predominantly glycine (G, Gly) residues, such as those having G4S (Gly-Gly-Gly-Gly-Ser) repeats (SEQ ID NO: 21) or G3S (Gly-Gly-Gly-Ser) (SEQ ID NO: 22) where the number of repeats is typically from one to twelve, may be used for this purpose.

The first polypeptide is an exogenous protein and the second polypeptide is a filamentous phage pVII or pIX protein, whereby the exogenous protein is fused to the amino terminus of the filamentous phage protein. Further, when the fusion protein is in the immature form, i.e., where the leader sequence has not been processed (removed), a fusion protein can also contain a amino terminal prokaryotic secretion signal, such as a wild-type or mutant pelB or ompA sequence (SEQ ID NO: 14 and 15, respectively) and the like as described herein.

In natural antibodies, the light chain polypeptide and the heavy chain polypeptide chains are encoded and expressed separately. The typical heterodimeric structure of the IgG class of molecules is dependent on the proper assembly of and formation of disulfide linkages among and between the four polypeptide chains, two heavy and two light chains, of the molecule. Thus, in the present invention, the assembly of the dimeric Fc-portion of the antibody and/or the association of the light chains, when present, recapitulates the natural process of antibody formation insofar as the individual domains of the protein self-associate and form disulfide linkages therebetween.

In one embodiment, the Fc-containing protein to be displayed on the surface of the filamentous phage particle is a natural antibody and a dicistronic vector is constructed for the expression of a Fc-construct-pIX fusion protein and a separately encoded and expressed antibody Lc or antigen binding domain which will self-associate. Antigen-binding proteins of the invention can have binding sites for any epitope, antigenic site or protein. Preferred antigen-binding proteins neutralize activation of receptor proteins by direct binding to the receptor or by binding to their cognate ligand(s). Generally, the antigen binding domain will be formed of an antibody Lc and an antibody Hc variable domain fused to the natural antibody Hc sequence comprising the Fc domains. In another embodiment, the pIX-fusion protein includes a scFv linked to the Fc-domain. In another aspect of the invention, the antigen binding sites of the heavy and light chains comprising the scFv may be varied to provide two different binding specificities thereby making the self-assembled disulfide linked construct protein displayed in the phage surface a bispecific and bivalent molecule. For example, substituted for the $V_L$ and $V_H$ domains of an IgG molecule are scFv domains of different specificity such that the resulting molecule, and is capable of binding to two different epitopes simultaneously. Other methods of creating bispecific antibody molecules having multiple variable domain pairs are taught in US20020103345A1 which could be displayed on phage particles using the methods of the present invention incorporated herein by reference.

In one embodiment the antigen binding or receptor binding domain is not derived from an antibody domain but is a known or random peptide sequence fused to the Fc-domain. The bioactive peptides, linked to the alternate chains of the Fc, optionally with a linker moiety therebetween, may be the same or different. The bioactive peptides may be linked to intervening linker or to the Fc from any residue on the peptide so long as the final conjugate displays the desired bioactivity. Bioactivity may be measured by in vitro assays, for example binding activity, by in vivo activity such as in animal models of disease, or by the response of a subject following administration of the conjugate.

Applicants co-pending applications WO04/002417; WO04/002424; WO 05/081687; and WO05/032460 describe a structure referred to herein as a MIMETIBODY™ structure, each of which references are entirely incorporated herein by reference, and which structures are included as dimeric disulfide-linked structures of the present invention, which may be fused to the pIX or pVII phage coat protein and displayed on the outer surface of the phage particle.

In one embodiment, the MIMETIBODY comprises a pair of bioactive peptide-linker-hinge-CH2-CH3 polypeptides, the pair linked by association or covalent linkage, specifically, a Cys-Cys disulfide bond. The bioactive peptide may be on (of?) any length and be a naturally occurring sequence derived from any species or be an artificial sequence. The peptides will generally be encoded by the phagemid vector and fused to the Fc-portion of the construct for display on the phage particle. One example of such a composition comprises an EPO-mimetic peptide as the bioactive peptide. Thus, an EPO-mimetic CH1-deleted MIMETIBODY mimics the antibody structure with its inherent properties and functions, while displaying a therapeutic peptide and its inherent or acquired in vitro, in vivo or in situ properties or activities. Other constructs of similar structure are also encompassed by the invention where the peptide has no known bioactivity but it present to function as marker, a tag, an antigen, or provides for conjugation of a reporter group, a chelating group, or the like.

In a typical embodiment an Fc-containing fusion protein or "MIMETIBODY™" comprises formula (I) which is absent some or the entire immunoglobulin CH1 domain:

$$V1_o\text{-}Pep_a\text{-}Flex_n\text{-}V2_m\text{-}Hinge\text{-}CH_2\text{—}CH_3 \tag{I}$$

where Pep represents a bioactive peptide or polypeptide capable of specifically recognizing a target, Flex is an optional flexible linker polypeptide that provides structural flexibility by allowing the MIMETIBODY to have alternative orientations and binding properties, V1 and V2 are bracketing sequences, Hinge is at least a portion of an immunoglobulin hinge region, e.g. SEQ ID NO: 1-4, CH2 is at least a portion of an immunoglobulin CH2 constant region, e.g. SEQ ID NO: 5-8, CH3 is at least a portion of an immunoglobulin CH3 constant region, e.g. SEQ ID NO: 9-12; m, n and o can be zero or can be an integer between 1 and 10, and a can be an integer from 1 to 10. The Pep sequence can optionally include of sequences for the purposes or stabilization or any number of biophysical functions. In a typical embodiment, the bracketing sequences are derived from an antibody variable (V) domain such as a Vh framework and V1 is the sequence QIQ and V2 represents a sequence derived from an immunoglobulin J gene domain and is GTLVTVSS (SEQ ID NO: 13). The resulting polypeptide can be linked to other polypeptides by association or covalent linkage, such as, but not limited to, a Cys-Cys disulfide bond.

The level of expression of pIX fusion proteins can additionally be controlled at the transcriptional level. The fusion proteins are under the inducible control of the Lac Z promoter/operator system (see FIG. 1). Other inducible promoters can work as well and are known by one skilled in the art. For high levels of surface expression, the suppressor library is cultured in an inducer of the Lac Z promoter such as isopropylthio-β-galactoside (IPTG). Inducible control is beneficial because biological selection against non-functional pIX fusion proteins can be minimized by culturing the library under non-expressing conditions. Expression can then be induced only at the time of screening to ensure that the entire population of antibodies within the library are accurately represented on the phage surface.

The vector encoding the dimerizing polypeptide phage coat protein fusion protein may include a translational termination codon at the junction of the exoprotein and phage coat protein coding regions. When expressed in a bacterial cell carrying a corresponding translation termination suppressor, the fusion protein is produced. When expressed in a bacterial cell without the corresponding suppressor, free exoprotein is not produced.

Method of Using the Invention

Using the phage vectors exemplified herein as a starting point, the proteins can be variegated at specific, discrete residue positions or at regions such as N-linked glycosylation sequence, commonly referred to as an NXT sequence, using directed mutagenesis to generate a library of molecules. Particularly useful is a modified Kunkel mutagenesis method which can be used to generate billions of E. coli colonies each harboring a different exoprotein sequence. While efficient, the percentage of non-mutagenized parental DNA increases when generating highly complex sequence libraries. In addition, technical limitations of synthesis of long oligonucleotides reduces the effectiveness of the method when used to make libraries containing sequence diversities in distant regions. To overcome these limitations, additional techniques of generating oligonucleotides greater than 350 bases can be used. These techniques include use of a mega-primer and creation of a stem-loop sequence containing a restriction enzyme recognition site in the mutagenesis template in combination with the standard Kunkel mutagenesis method (Kunkel at al. 1987 Methods Enzymol 154: 367-382) as described in US20050048617. Compared to other library technologies, such as restriction cloning (Marks et al., 1991 J. Mol. Biol. 222:581-597; Griffiths et al. 1994 EMBO J. 13, 3245-3260; Hoet et al. 2005 Nature Biotechnol 23, 344-348), phage recombination (Gigapack, Invitrogen), and sequence specific recombination, the improved Kunkel based method is significantly more effective in generating a sequence diverse library (greater than $10^9$) and is more versatile for introducing sequence diversity in any location in the targeted DNA.

The display of an Fc-containing protein on filamentous phage is particularly useful where it is desired to screen a large population of such molecules for desired binding characteristics. In one embodiment, bacterial cells expressing the Fc-construct-pIX protein fusion are infected with an M13 variant which allows for preferential packaging of vector DNA carrying the Fc-construct-pIX fusion gene into phage particles. Each resulting phage particle displays a particular Fc-construct-pIX fusion protein and contains a vector which encodes the Fc-construct-pIX fusion. The population of such phage particles can be enriched for desired binding characteristics by a panning procedure. Typically, desired particles are immobilized on a solid surface coated with an antigen to which the desired phage particles can bind. The bound particles are collected and used to further infect bacterial cells. The panning procedure is repeated to further enrich for desired binding characteristics.

In one embodiment, the phage library is used to screen variants of the Fc-portion of the molecules for enhanced, decreased, or altered binding to natural or recombinant Fc-receptors, such as FcRgammaIII (CD16), FcRgammaII (CD32), and FcRgammaI (CD64).

Phage and other antibody display methods afford the opportunity to manipulate selection against the antigen or receptor target in vitro. One particular advantage of in vitro selection methods is the ability to manipulate selection procedures to obtain antibodies binding to diverse sites on the target protein. Alternatively, whole cells may be used to select binders.

Phage libraries simplify the retrieval of genetic material associated with functional attributes, however, multistep panning strategies are required to isolate the best candidate from the library. Domain or epitope directed pannings have become a routine way of selecting antibodies that bind to a target protein. Such selections have primarily been achieved by employing a stepwise selection of antibodies utilizing methods known variously as selective panning, de-selective panning, ligand capture, subtractive panning or pathfinder selection.

In subtractive panning, target(s) with overlapping but not completely identical binding sites can be used to de-select unwanted binders. This strategy has been used to identify binders even to unknown antigens as in the use of normal cells to de-select binders to cancer cells. Alternatively, naturally occurring proteins with some common domains or structure are used in sequential or competition selection to obtain antibodies binding to sites that differ or are common among the related antigens. In some cases, naturally occurring proteins such as related chemokines or a mutated version of a protein can be used in subtractive panning.

Ligand-capture directed panning is analogous to an ELISA sandwich assay in that an immobilized antibody to an irrelevant and non-adjacent epitope is used to capture and present the preferred binding face of the target ligand for phage panning (U.S. Pat. No. 6,376,170). Others have used competing antibodies to selectively mask the antigen at other than the desired target domain (Tsui, P. et al. 2002. J. Immunol. Meth. 263:123-132). Pathfinder technology uses monoclonal and polyclonal antibodies, as well as natural ligands conjugated directly or indirectly to horseradish peroxidase (HRP). In the presence of biotin tyramine these molecules catalyze biotinylation of phage binding in close proximity to the target antigen, allowing specific recovery of 'tagged' phage from the total population using streptavidin. In this way, phage binding to the target itself, or in its immediate proximity, are selectively recovered (Osborn, J. K. et al. 1998. Immunotechnol. 3: 293-302). These methods, variations of the methods, and other methods known to those skilled in the art may be employed to query the libraries of pIX-exoproteins of the present invention.

While having described the invention in general terms, the embodiments of the invention will be further disclosed in the following examples that should not be construed as limiting the scope of the claims.

EXAMPLE 1

Display of an Fc-Fusion Protein on pIX

A. Phagemid Vector Construction

Phagemid vector, pCGMT9 (Gao et al., Proc. Natl. Acad. Sci. 96:6025-6030, 1999, U.S. Pat. No. 6,472,147) served as the backbone for the development of a phagemid pIX display vector capable of inserting heavy chain constant domains for phage display via pIX fusion. In this phagemid, origins of replication for *E. coli* (colE1) and filamentous phage (f1) are present, along with a beta-lactamase gene conferring resistance to ampicillin.

The pIX phagemid vectors for displaying Fc-containing proteins, including MIMETIBODY™ molecules, were constructed based on the Gao vector which had been adapted for bicistronic expression, pCNTO-Fab-pIX, as disclosed in WO2009/085462 and FIG. 1. Unlike the strategy used for Fab phage display in which a soluble light chain is expressed in the same cells and associates with the tethered polypeptide, no soluble Fc was expressed (FIG. 2A).

The Fab light chain sequence in the vector was deleted. The Fab heavy chain sequence in the vector was replaced with either Fc or a construct or a MIMETIBODY™ construct. Construction of the phagemid vector Fc containing the cysteine pair containing core hinge was achieved as follows. The Fc gene segment encoding the core hinge, CH2, and CH3 of the human IgG1 was amplified from an Fc-containing plasmid by PCR. An NcoI restriction site was incorporated into the 5' primer end and a SacII restriction endonuclease site at the 3' primer end. The PCR amplified DNA fragment and the phagemid vector (pCNTO-Fc-pIX core Hg) were digested with the NcoI and SacII restriction endonucleases. Digested products were purified, ligated using a rapid ligation kit, and transformed into DH10B *E. coli*. Transformed clones were screened using DNA sequencing, and one that showed the correct sequence was then transformed into TG-1 *E. coli* for phage preparation.

A pIX phagemid vector (p2467) encoding an EMP-1 (SEQ ID NO: 16) Fc (SEQ ID NO: 17) construct, described in U.S. Pat. No. 7,393,662 and SEQ ID NO: 88 therein, and called an "EPO MIMETIBODY™" or CNTO530, was constructed by replacing the Fc encoding sequence with the sequence encoding the complete CNTO530 fusion protein via restriction enzyme cloning. The CNTO530 coding sequence was amplified from plasmid p2467 by PCR. The restriction endonuclease sites NcoI and SpeI were included in 5'- and 3'-end primers, respectively. The PCR product and phagemid vector, pCNTO-Fc-pIX core Hg, were digested with NcoI and SpeI, purified, ligated using a rapid ligation kit, and transformed into DH1OB *E. coli*. Transformed clones were screened by DNA sequencing and one with the correct sequence was transformed into TG-1 *E. coli* for phage display.

B. Preparation and Characterization of the Recombinant Phage

TG-1 *E. coli* transfected with phagemid vectors were grown in liquid culture to $OD_{600}$=0.5-0.6. VCSM13 helper phage stock was added to the culture, and the infection proceeded as a static incubation at 37° C. for 45 minutes. Cultures were centrifuged to pellet the bacteria, resuspended in media supplemented with carbenicillin, kanamycin and IPTG and incubated at 30° C. for 12-16 hours with shaking at 250 RPM. The overnight culture was centrifuged and the phage-containing supernatant was transferred to a fresh tube to which a one-tenth volume of cold sodium chloride/PEG solution (what concentration NaCl and PEG? or just say PEG precipitated using standard methods (ref)) was added. Each tube was mixed and incubated on ice for approximately three hours with occasional mixing, after which the tube was centrifuged to pellet phage. Phage pellets were carefully resuspended in PBS, transferred to a new tube, and centrifuged a second time to remove any remaining cellular debris. Purified phage were stored in aliquots at −80° C. Spot titration was performed to estimate the phage titers as colony forming units (cfu) per milliliter.

C. Characterization of Displayed Proteins

Confirmation of Display of Fc and Peptide-Fc Constructs.

Two individual preparations of phages were used in the experiments. To detect the Fc-bearing or CNTO530 bearing phage, black ELISA plates were coated with either an anti-human Fc gamma specific polyclonal antibody or an anti-EMP1 peptide monoclonal antibody (CNTO 3443). Coated plates were blocked with 5% milk in TBST and washed with TBST. Helper phage, Fc- or CNTO530 recombinant phage were added to the plates, incubated for one hour at room temperature, and washed to remove unbound phage. Bound phage were detected with an HRP-conjugated anti-M13 mAb and chemiluminescent substrate. The captured phages were detected using the HRP-conjugated anti-pVIII mAb. The helper phage and, in the case of the CNTO530 bearing phage, Fc recombinant phage without EMP1 peptide were used as negative controls.

Protein A binding.

Purified recombinant Protein-A was coated on the blackwell ELISA plates overnight at 4° C. The coated plates were blocked with 5% milk in TBST and washed with TBST. Appropriate dilutions of helper phage or Fc-displaying phage were added to the plates. Plates were incubated for one hour at room temperature and washed to remove unbound phage. To block any remaining unoccupied Fc binding sites on the coated Protein-A, a human-antibody derived Fc was added to the plates at saturating concentrations. After 30 minute incubation, bound phage was detected with an HRP-conjugated anti-M13 mAb and chemiluminescent substrate.

FcRn Binding.

FcRn (the neonatal Fc-receptor), allows antibody reuptake, compartmental translocation, and recirculation and, thus, prolongs the circulating half-life of antibodies. Fc binding to FcRn is pH-dependent and the ELISA binding assay was conducted accordingly. FcRn-bound phage was captured on Neutravidin coated 96-well plates and detected with the HRP-conjugated anti-pVIII mAb. Briefly, black-well ELISA plates were coated with Neutravidin and blocked with a 50/50 mixture of SuperBlock T20 (TBS) and Chemiblocker. The plates were washed with TBST and biotinylated FcRn was captured or one hour. Appropriate dilutions of helper phage or Fc-displaying phage, were prepared at pH=6 or pH=7.5 in TBST. Unbound FcRn was washed from the plate phage were added and incubated for one hour. Alternatively, biotinylated FcRn was mixed with phage for one hour at room temperature prior to addition to the plate. To block the remaining unoccupied Fc binding sites on the coated FcRn, a human antibody-derived Fc was added to the plates at saturating concentration. Bound phage were detected with an HRP-conjugated anti-M13 mAb and chemiluminescent substrate.

D. Results

Figure 3:
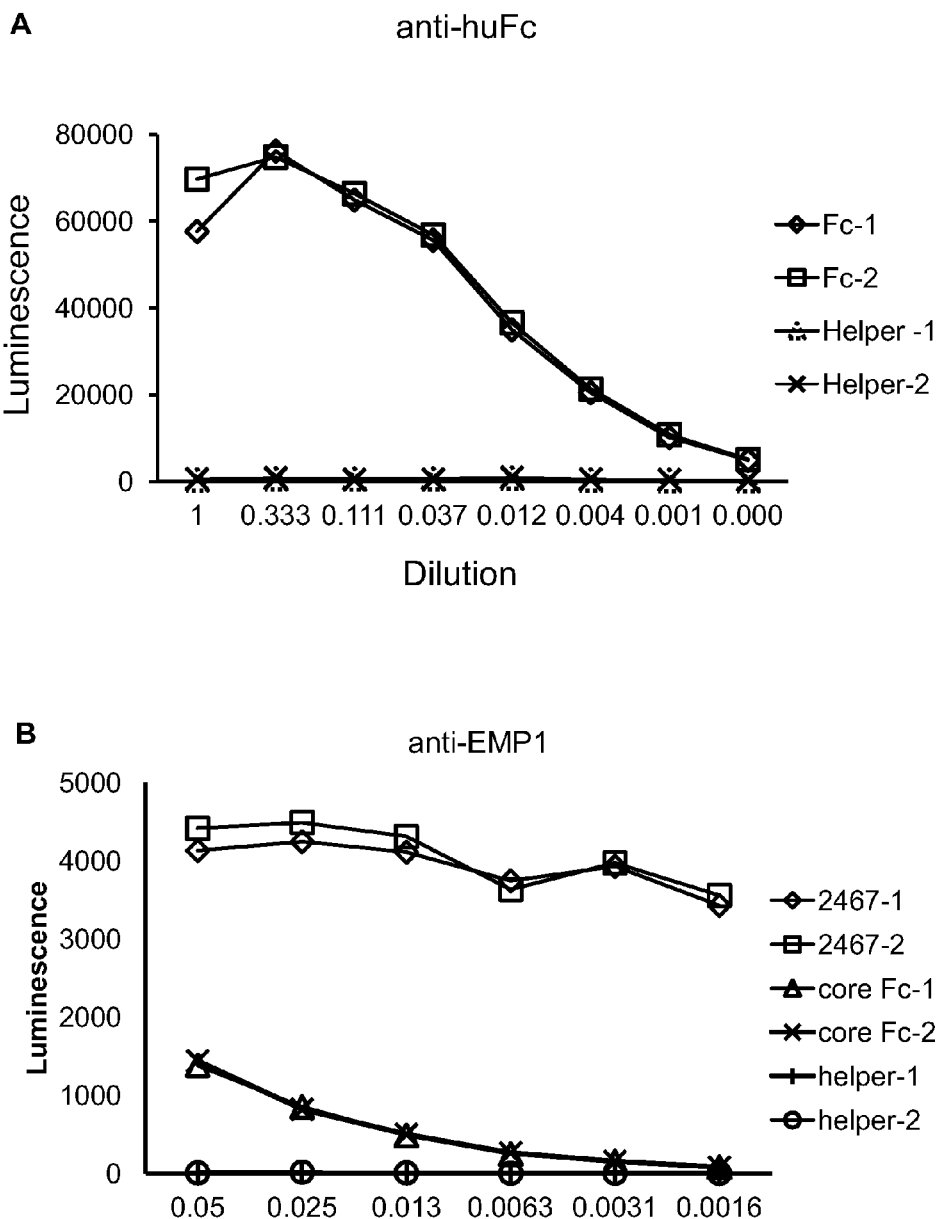
FIG. 3 A-B are graphs showing the results of ELISA on recombinant phage particles constructed as described in Example 1 demonstrating the increase of Fc-fusion proteins (A) or EMP-1-Fc (B) where recombinant phage particles were captured on a plated coated with anti-Fc Mab (A) or with CNTO 3443, an anti-EMP1 mAb (B), and the captured phages were detected using the HRP-conjugated anti-pVIII mAb. The helper phage were negative controls as was Fc phage in B. Two individual preparations of phages were used in the experiments.

The ELISA assay was designed to show the proportion of phage displaying Fc, as the phage displaying Fc were captured using an anti-Fc antibody and detected using an anti-pVIII antibody (FIG. 3A). The strong signal observed for Fc recombinant phage and lack of observed signal for helper phage demonstrates that Fc was efficiently displayed on the phage surface. EMP1-fusion protein construct, CNTO530, display was confirmed using a EMP-1 specific antibody as the capture ligand as shown in FIG. 3B. To confirm that the Fc-region retained the appropriate biologic activity and, thus, was dimeric, specific binding assays were conducted: protein A binding, and FcRn binding. As shown in the FIG. 4, phage with Fc displayed on its surface bind to protein-A while control helper phage that lack the Fc do not. The chemiluminescent signals for Protein A binding are similar to that of the Fc-displaying phage captured with human immunoglobulin gamma specific polyclonal antibody, suggesting that the majority of phage displayed Fc are folded into a conformation competent for binding to Protein A.

Figure 5:
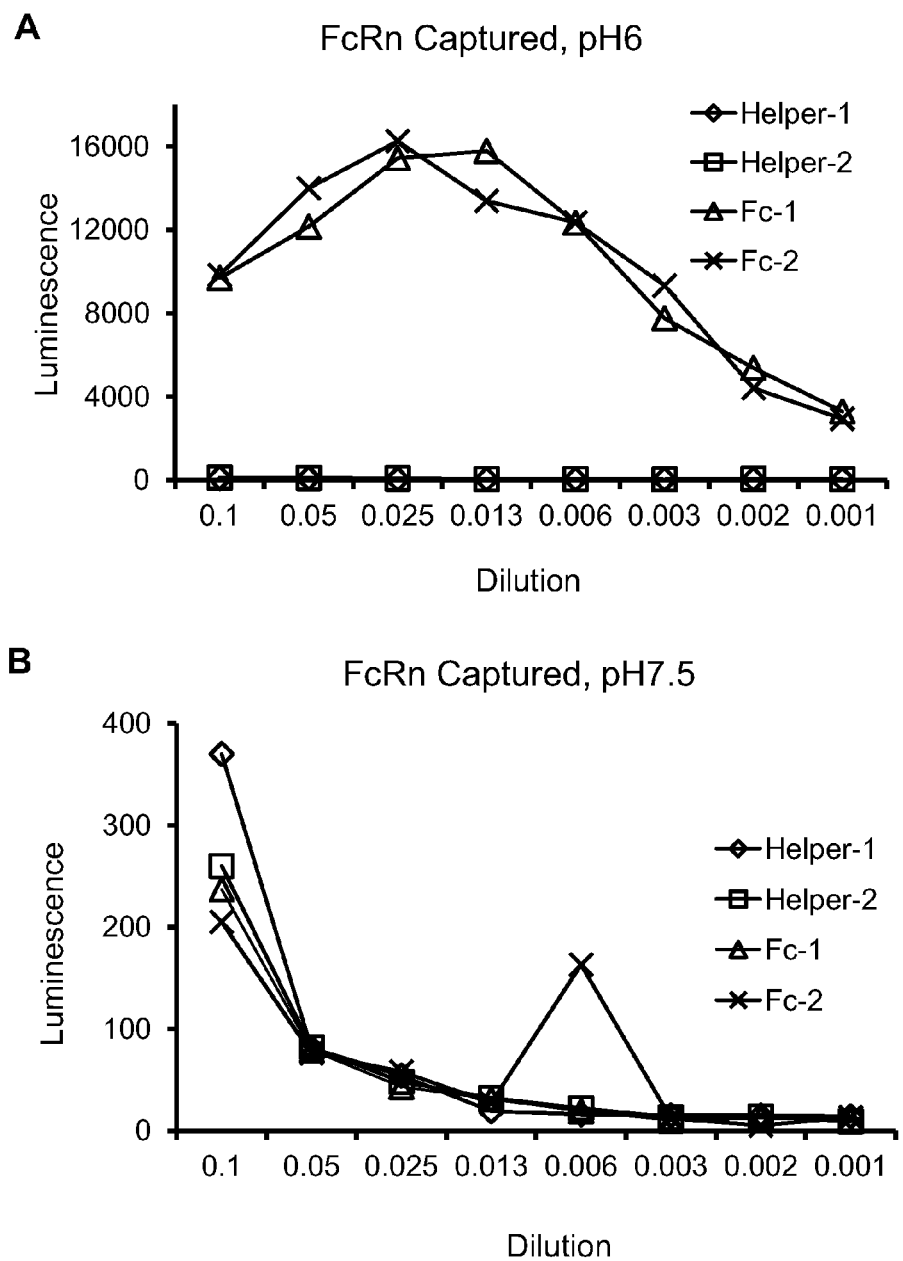
FIG. 5A-B are graphs from a FcRn binding assay conducted at the optimal binding acidity, pH 6.0 (upper) and under the non-specific binding condition, pH 7.5 (lower).

Fc binds to FcRn at pH 6.0 but looses several orders of magnitude of binding affinity at pH7.5. Phage was incubated with biotinylated FcRn at either pH 6.0 (FIG. 5A) or pH 7.5 (FIG. 5B). As demonstrated by the strong signal observed at pH 6.0, the Fc recombinant phage bound efficiently to FcRn at pH 6.0. In contrast, the same phage showed a much lower signal at all concentrations tested. Therefore, pH dependent binding was retained for Fc displayed using a pIX phagemid system.

Figure 4:
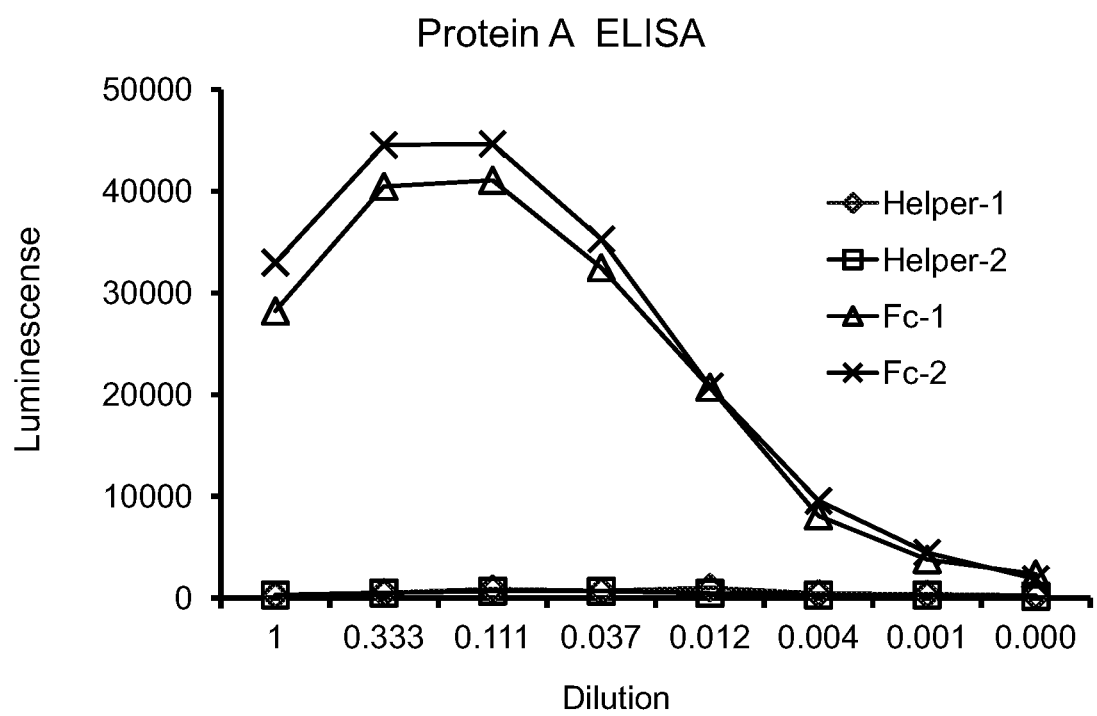
FIG. 4 is a graph from a binding assay showing that the Fc-domains displayed on the phage are capable of binding to protein A.

IgG and other Fc-containing molecules form homodimers via interaction of CH3 domains. The homodimer is stabilized by two disulfide bounds in its core hinge region. Because the Fc phagemid display vector encodes only a single copy of the Fc gene, we examined the aggregation state of the displayed Fc via Western Blot. Concentrated phage particles were loaded directly onto the SDS gel under reducing or non-reducing conditions. As shown in FIG. 4, under non-reducing conditions, the majority of the protein migrated as a dimer with the molecular weight around 62 kD, as expected for the dimer Fc-pIX fusion protein. Conversely, under reducing conditions, the majority of the Fc-pIX protein migrated as a monomer of 31 kD. Thus, the majority of Fc molecules displayed on the phage surface are homodimeric and covalently linked with disulfide bonds, in the same manner as IgG or other Fc containing molecules.

E. Summary

The strong signal observed for the recombinant phage together with the lack of signal for helper phage demonstrates that an EPO-receptor agonist (EMP-1) Fc construct was efficiently displayed as demonstrated by the detection of the peptide as well as Fc on phage particles. The data indicates that the Fc-containing proteins were displayed effectively on phage as homodimers which have characteristic conformational features allowing binding to natural ligands.

EXAMPLE 2

Peptide-Fc Fusion Library

To generate a Peptide-Fc fusion library, a template phagemid, which contains a hairpin loop at the site of random amino acid sequences, was generated. The hairpin was designed in such a way that a unique restriction site, XbaI, was placed where the hairpin formed double-stranded DNA. This would later be used to remove template DNA via restriction digest with XbaI, thereby reducing phage packed with the template phagemid in the final constructed library. Double-stranded template plasmids were transformed into a dut-lung-E. coli host strain, CJ236, as passage through this cell line causes incorporation of uracil into the ssDNA. The uracil containing ssDNA template is then degraded by enzymes of the final library host cell. A single colony harboring the plasmid was grown in a liquid culture that was subsequently infected with VCS-M13 helper phage. The phage was precipitated with PEG plus saline and used for purification of single strand DNA.

DNA libraries were generated using a modified Kunkel mutagenesis protocol. Oligomers encoding the randomized library nucleotides, as well as 5' and 3' flanking sequences, were enzymatically phosphorylated using T4 kinase. Phosphorylated oligos were annealed to their respective ssDNA templates using a three-step temperature reduction program. Second strand synthesis was performed by adding T7 DNA polymerase and T4 DNA ligase to the reaction mixture to form covalently-closed circular DNA (CCC-DNA). The CCC-DNA was purified and then digested with XbaI at the hairpin sequence to cleave the template DNA for reducing the background. Both pre- and post-digestion CCC-DNA products were examined by agarose gel electrophoresis to evaluate the quality of the library preparation prior to its introduction into cells. The ligation mixture was then transformed to the MC1061F' host cell line (E. coli).

The four pIX displayed libraries were constructed in which seven (A1 and A2) or eight (B3 and B4) random amino acids loop constrained with a disulfide bond each in two Fc-containing MIMETIBODY™ constructs (See Formula 1 above) where the linker is GGSG (SEQ ID NO: 23) or GS, the V region J-piece (SEQ ID NO: 13) is present or absent and the hinge comprises either the core amino acids of CPPC (SEQ ID NO: 24) an IgG1 type hinge with or without adjacent sequences. These two variant Fc-regions are represented are shown below where the residues differing from natural occurring IgG4 are underlined, and which are represented by SEQ ID NO: 17 and 18. Two more random amino acids were added at the each end of the constrained loop.

A. 7NNK libraries (XXCXXXXXXXCXX) (SEQ ID NO: 25)

1) Fc=mutant IgG4 with V-region and full hinge (SEQ ID NO: 18). 2) Fc=mutant IgG4 with hinge core (SEQ ID NO: 17)

B. 8NNK libraries (XXCXXXXXXXXCXX) (SEQ ID NO: 26)

3) Fc=mutant IgG4 with V-region and full hinge (SEQ ID NO: 18)

4) Fc=mutant IgG4 with hinge core (SEQ ID NO: 17)

For each library generated, a total of 31 electroporations were performed. After removing a small aliquot to titer for transformation efficiency, outgrowth cultures were immediately scaled up to a one-liter culture volume that was grown to an $OD_{600}$ of 1.0. At this point the culture was split: one-tenth of the culture was infected with VCSM13 helper phage to generate phage libraries while the bulk of the culture was used to establish glycerol stocks of the bacterial libraries. The phage-infected culture was once again expanded to increased scale and grown overnight. Phage libraries were purified from the culture supernatant using PEG/NaCl precipitation on ice. Resultant phage titers were estimated using spot titration to measure the number of colony forming units per milliliter (cfu/mL). Aliquots of the $1 \times 10^{-9}$ and $1 \times 10^{-10}$ dilutions from the spot titration preparation were spread onto LB media plates supplemented with glucose and carbenicillin to isolate single colonies. For each library, ninety-six single colonies were sequenced to evaluate the diversity and functionality of the final phage library. This was also used to determine how much background contamination residual template provided.

Summary

Two Fc-scaffolds, one with a short flexible glycine-serine linker (GS), core hinge, CH2 and CH3 (represented by SEQ ID NO: 17) and the other with a flexible glycine-serine linker (GGGS), a portion of the Vh domain, a mutated IgG4 hinge, CH2, and CH3 (represented by SEQ ID NO: 18); produced libraries with complexity of about $1-3 \times 10^9$. Sequencing of 96 clones from each library showed no sequence of the clones was identical, indicating that the diversity of the library was good.

EXAMPLE 3

Full IgG Display on Phage Particles

A. Vector Design.

The full IgG display phagemid (vDR47, FIG. 2B) was construct using the pCNTO Fab IX construct shown in FIG. 1, and as described in WO2009/085462, which comprised a Vh and CH1 (SEQ ID NO: 19) domain of the heavy chain. Sequences encoding the hinge, CH2 and CH3 domains of a human IgG1 (SEQ ID NO: 20) were added as well as a variant pelB signal sequence, with a single mutation from the wild-type sequence, P6S (SEQ ID NO: 14), causing a significant improvement in peptide display on pVII minor coat protein and protein secretion (applicants co-pending application) and the vector does not have a lacI gene but does have a lac promoter.

B. Characterization of Constructs Used for Full IgG Display.

A panel of test constructs was made to assess the display of full IgG on pIX. Antibodies to IL13, designated 6-2 and 16-7, and an anti-cytokine antibody 9-4 were chosen as prototypes for constructing the new full IgG molecules. To determine the effect of different codon usage, two constructs were made for each of the anti-IL13 antibodies, one with human codon optimization and one with E. coli codon optimization. Table 1 lists the vector designation for the five full IgG test constructs. Optimized genes were synthesized and assembled into double stranded DNA as described in U.S. Pat. Nos. 6,670,127 and 6,521,427. In addition, the EMP-1 Fc fused to pIX (Example 1) was included as a control as it contains IgG Hinge, CH2 and CH3 domains but no light chains.

TABLE 1

Test constructs for full IgG Display

| pDR# | Isotype | Codon Usage | Description | Antigen Specificity |
|---|---|---|---|---|
| pDR2129 | huIgG1/HuKappa | Human codon | 6-2 full IgG | h IL13 |
| pDR2130 | huIgG1/HuKappa | Human codon | 16-7 full IgG | h IL13 |
| pDR2131 | huIgG1/HuKappa | E. coli codon | 6-2 full IgG | h IL13 |
| pDR2132 | huIgG1/HuKappa | E. coli codon | 16-7 full IgG | h IL13 |
| pDR3041 | huIgG1/HuKappa | Human codon | 9-4 full IgG | h IL17A |

C. Phage Production

The full IgG display constructs described in section B above were transformed into two different F' E. coli strains, TG-1 and XL-1 blue, according to standard protocols. The reason for testing these two strains is their difference in growth rate, which hypothetically could affect the packaging and display of the full IgG pIX fusion protein. Individual transformants were picked and grown over night in 2XYT media supplemented with Carbenicillin (always used at 100 µg/ml). The overnight culture (500 µl) was then used to inoculate 25 ml 2XYT/Carbenicillin and the culture was grown at 37° C., 250 rpm, until OD (600 nm) reached 0.5. The bacteria were infected with 1011 pfu/ml of VCSM13 helper phage (Stratagene, La Jolla, Calif.) during a 30 min incubation at 37° C. with no shaking followed by a centrifugation step at 3,000 rpm for 15 minutes. At this step, the standard protocol calls for the induction of the bacterial culture with 2XYT/Carbenicillin/IPTG (1 mM). However, we divided the cultures into two and added 1 mM IPTG to one and not to the other, with the hypothesis that the leakiness of the system would suffice to produce the fusion protein with subsequent phage packaging. In summary, for each construct, four different phage preparations were made: (i) TG-1 with IPTG (ii)

TG-1 without IPTG (iii) XL-1 blue with IPTG (iv) XL-1 blue without IPTG. The cultures were grown over night at 30° C. at 250 rpm and the next day, spun down at 3,000 rpm for 15 minutes, followed by the precipitation of the phage supernatant in PEG/NaCl. After 2 hours on ice, the precipitated phage were spun down at 10,000 rpm, 15 min, and the phage pellet was resuspended in 2 ml PBS. The phage prep was further clarified of any remaining bacterial pellet by a spin at 10,000 rpm for 10 min and stored in 2 ml tubes at 4° C.

D. Phage Titers

The phage titers were determined according to standard protocols. Briefly, TG-1 cells were grown in 2XYT until OD (600 nm) reached 0.5. Phage preparations were serially diluted in PBS in a 96 well plate and TG-1 cells were added to the phage and incubated at 37° C. to allow infection. After 30 min, a spot titration was carried out by dispensing 2 ul of each well onto LB agar plates containing 1% glucose and Carbenicillin. The plates were incubated at 37° C. overnight and the phage concentration in terms of colony forming units (cfu) per ml was determined Table 2 shows the results from the phage titration for all of the constructs and culture conditions. All clones produced high phage titers, between $10^{11}$-$10^{13}$ cfu/ml which were in the expected range and indicated that phage was produced efficiently.

TABLE 2

| Description | pDR vector | IPTG | TG-1 | XL-1 Blue |
|---|---|---|---|---|
| 6-2 IgG Human Codon | 2129 | – | 1.00E+13 | 2.00E+13 |
| | | + | 5.00E+12 | 5.00E+12 |
| 16-7 IgG Human Codon | 2130 | – | 2.00E+13 | 2.00E+13 |
| | | + | 2.00E+12 | 2.00E+12 |
| 6-2 IgG E Coli Codon | 2131 | – | 2.00E+13 | 2.00E+13 |
| | | + | 2.00E+13 | 2.00E+13 |
| 16-7 IgG E Coli Codon | 2132 | – | 2.00E+13 | 5.00E+12 |
| | | + | 1.00E+11 | 5.00E+11 |
| EMP-1 Fc Construct | 2467 | – | 2.00E+13 | 2.00E+13 |
| | | + | 2.00E+12 | 2.00E+12 |

E. IgG Domain-Specific Sandwich ELISAs to Assess Functional Display

In order to assess the display of the full IgG molecule on phage pIX, a series of sandwich ELISAs were set up. Black maxisorp plates were coated with 1 μg/ml of one of the following capture antibodies diluted in TBS; sheep anti-human IgG (Fd, CH1) antibody (The Binding Site, Birmingham, UK), mouse anti-human kappa light chains (Southern Biotech, Birmingham, Ala.), mouse anti-human IgG (CH2 domain) antibody (AbD Serotec, Raleigh, N.C.), and mouse anti-human IgG (CH3 domain) antibody (AbD Serotec). After blocking the plates with Chemiblocker (Chemicon/Millipore, Billerica, Mass.), plates were washed and phage were added at a concentration of 2×1011 cfu/ml (diluted in 10% Chemiblocker/TBST) and incubated for one hour. Plates were washed and HRP conjugated mouse anti-M13 antibody was added to the plates. After 30 min incubation, plates were washed and Chemiluminescence substrate was added to the wells and the plates were read in the Envision plate reader. FIGS. 7A-D show the results from the CH1 (FIG. 7A), Kappa (FIG. 7B), CH2 (FIG. 7C) and CH3 (FIG. 7D) sandwich ELISAs, respectively. Controls used in the ELISAs were phage displaying the Fab-pIX fusion of clone 6-2 in vDR10 (human codon optimized, made in TG-1 cells, with IPTG induction), an nonspecific scaffold protein-pIX fusion, or the CNTO530-pIX fusion. In the CH1 and Kappa ELISAs, the 6-2 Fab serves as a positive control, whereas the EMP-1 construct (CNTO530) molecule serves as a negative control. In the CH2 and CH3 ELISAs, the 6-2 Fab serves as a negative control and the CNTO530 molecule as a positive control. The scaffold protein phage serves as a negative control in all ELISAs since it does carry any antibody domains. The ELISAs assays were also performed with the addition of an anti-IL13 full IgG1 antibody as a soluble competitor at a concentration of 5 ug/ml in order to prevent binding of the phage to the different capture antibodies.

Figure 7A:
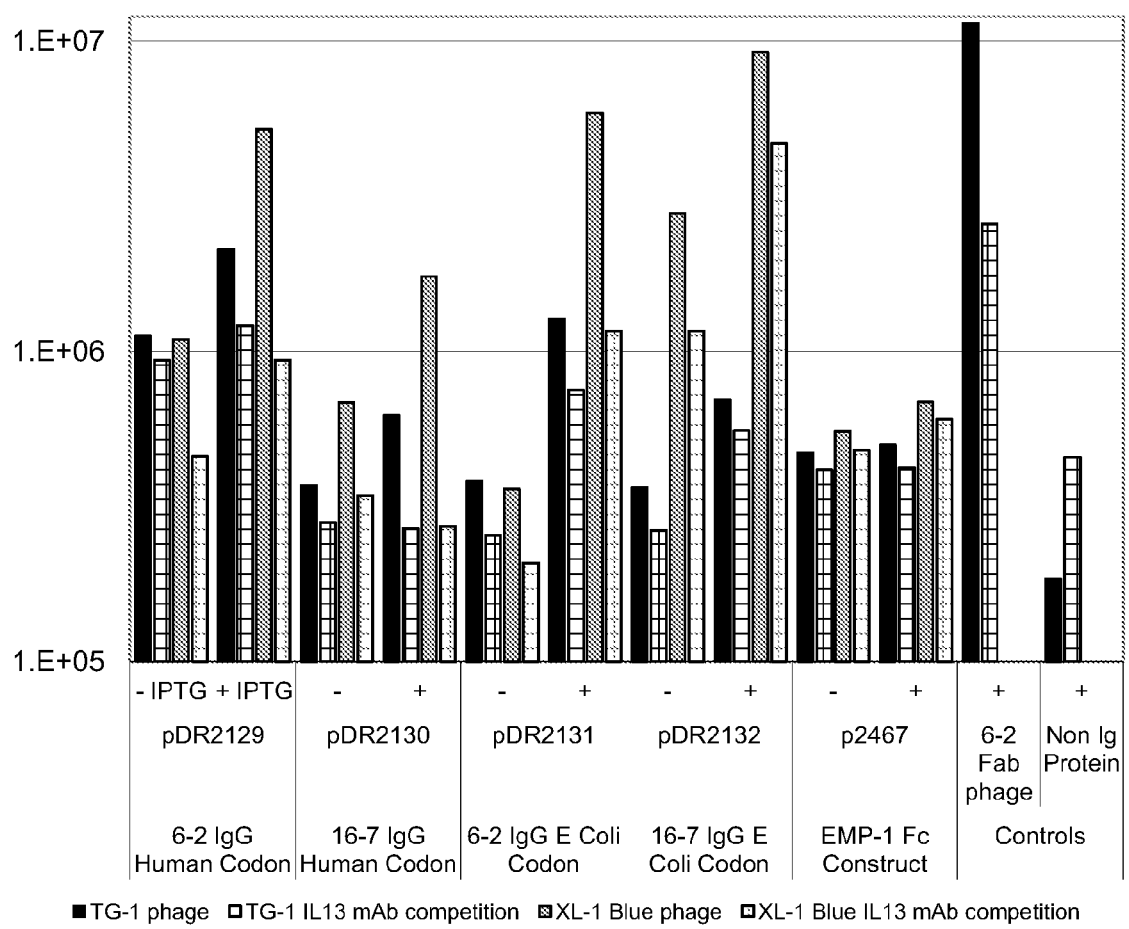
FIG. 7 A-D are column graphs showing the signal produced in an ELISA format for phage captured from the indicated preparations using various ligands specific for either antibody domains expressed on the phage, an expressed EMP-1-Fc construct, or the phage itself and cultured with or without the lac inducer IPTG: (A) Anti-Fd (CH1) antibody capture; (B) anti-kappa antibody; (C) anti-CH2 antibody; and (D) anti-CH3 antibody. The phage displaying 6-2 Fab or the non-immunoglobulin protein on pIX are included as negative controls.
Figure 7B:
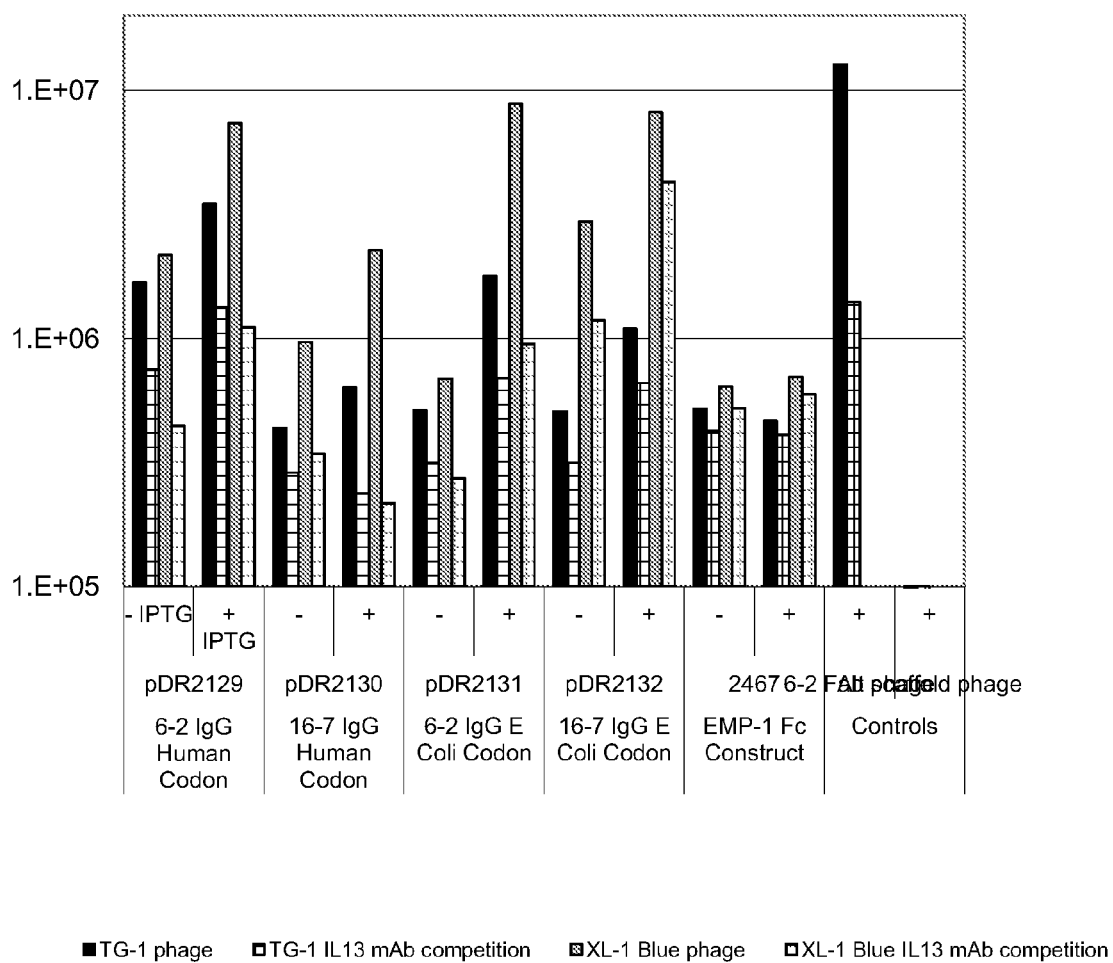
Figure 7C:
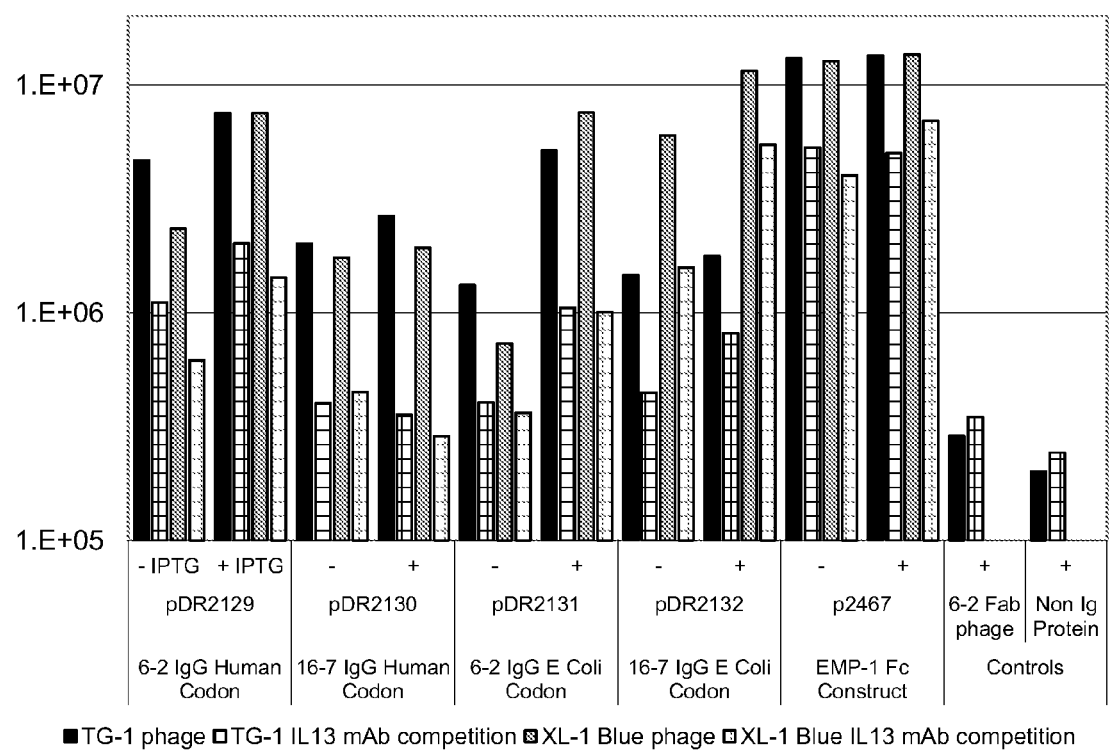
Figure 7D:
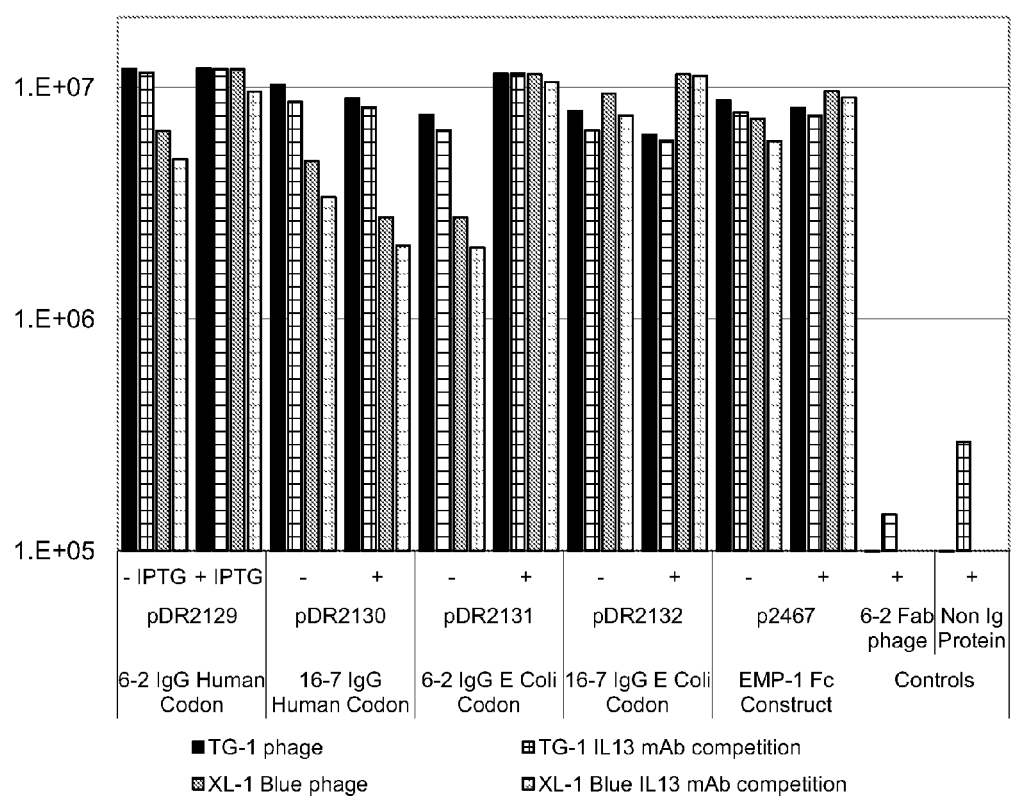

As shown in FIGS. 7A-D, phage was detected in all of the sandwich ELISAs, providing evidence that the phage were in fact displaying the different antibody domains on the surface. Phage produced in XL-1 blue cells had the highest signals and the addition of IPTG had a positive effect on the binding signal. The binding of phage can be inhibited by the addition of the soluble anti-IL13 antibody, which indicates specific interactions. However, the soluble anti-IL13 antibody could not compete off the interaction between phage and the CH3 domain (FIG. 7D). This was observed for both the full IgG-pIX fusions as well as for the EMP-1-Fc-pIX fusion (CNTO530).

F. Full IgG pIX Phage Binding to IL13

Figure 8:
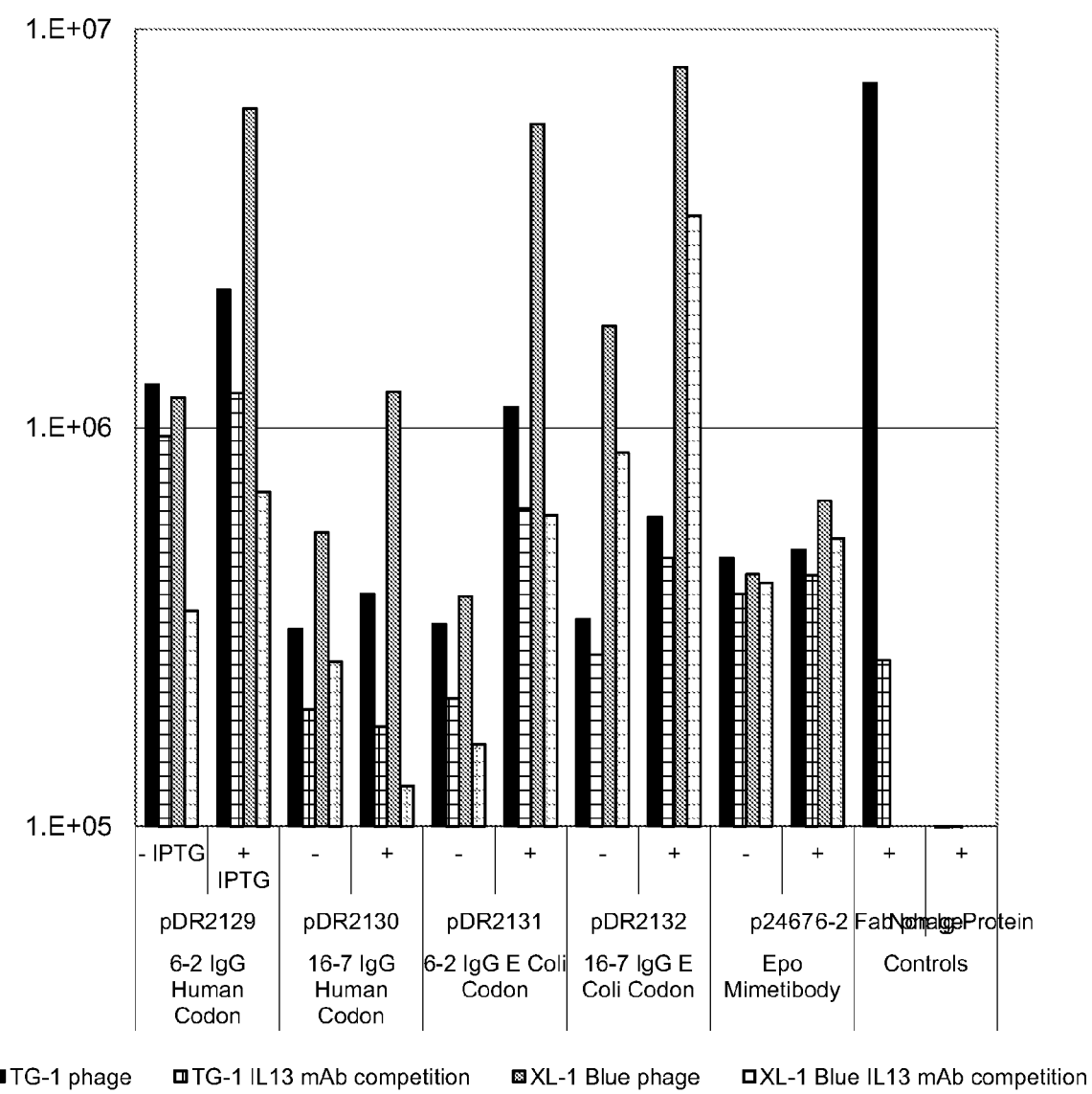
FIG. 8 is a column graph showing the signal produced in an ELISA format for phage captured from the indicated preparation using commercial anti-IL13 antibody and in the presence or absence of a competing soluble anti-IL13 mAb with the same specificity as the anti-IL13 IgG pIX (Checkered bars). The EMP-1-Fc construct is a negative control does not bind IL13 and the IL13 specific 6-2 Fab displayed pIX on phage as a pIX fusion is included as a positive control.
Figure 9A:
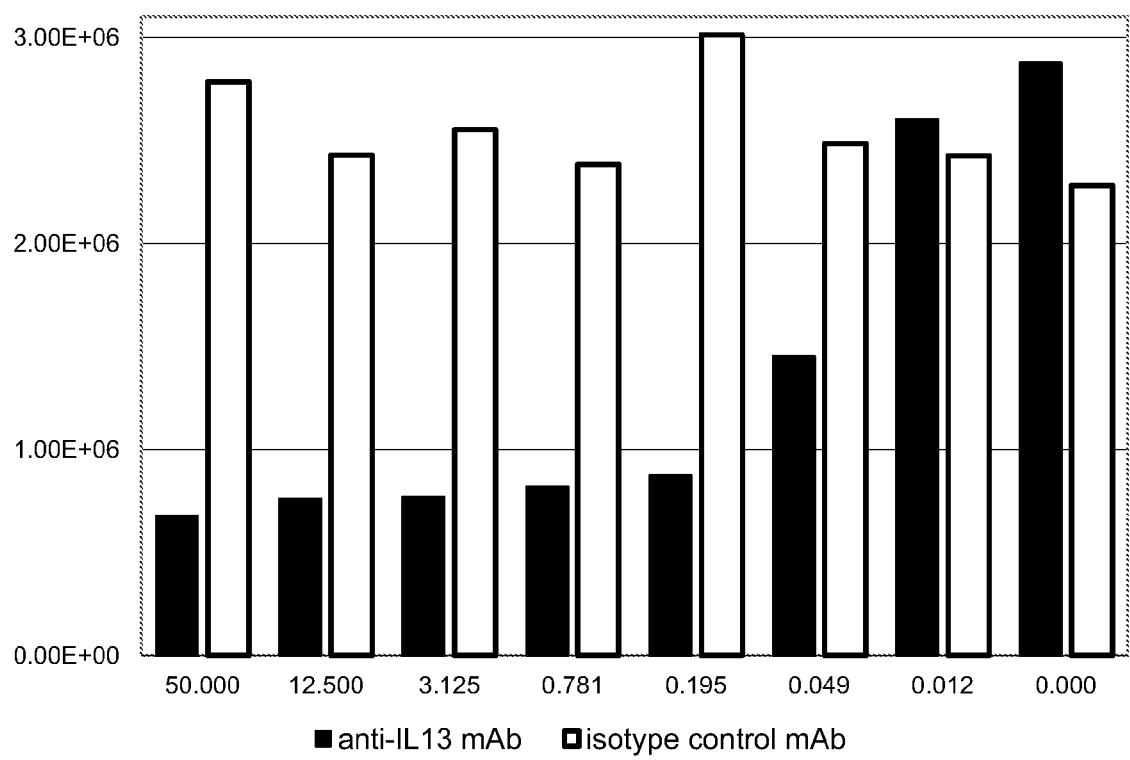
FIG. 9 A-B are column graphs showing the signal produced in an ELISA format for phage captured in plates by a commercial anti-IL13 antibody followed by the addition of increasing amounts of a competing anti-IL13 antibody (6-2 full IgG) on phage or a control antibody not specific for IL13 (anti-EMMPRIN) (A) and by IL13 captured in plates by a commercial anti-IL13 antibody followed by the addition of 6-2 Fab on phage. Increasing amounts of either an anti-IL13 mAb or an anti-EMMPRIN mAb was added (B).
Figure 9B:
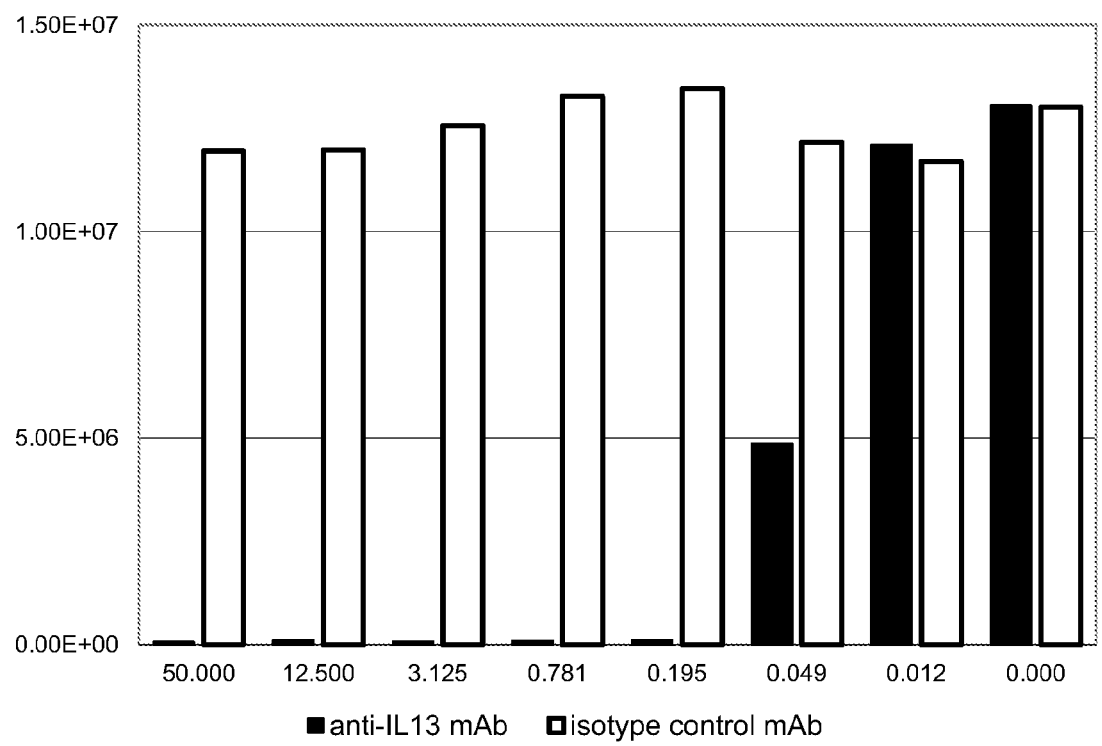

After demonstrating that all domains of the IgG molecule can be detected on the phage particles by the ELISAs, it was necessary to determine if the constructs also retained the ability to bind to their respective antigen. The IL13 binding ELISA was set up by coating black Maxisorp plates with 1 μg/ml of a commercial anti-IL13 antibody (mouse anti-human IL13, MAB213, R&D Systems). The MAB213 does not compete with 6-2 or 16-7 for binding to IL13 and thus is ideal as a sandwich ELISA capture antibody. After washing and blocking, biotinylated human IL13R130Q human (Peprotech) was added at 100 nM and incubated for one hour. Plates were washed and phage displaying full IgG versions of 6-2 and 16-7 on pIX were added at $2\times10^{11}$ cfu/ml, either alone or together with a soluble anti-IL13 antibody for competition. Bound phage was detected with HRP-conjugated mouse anti-M13 antibody and chemiluminescence was read in the Envision instrument. FIG. 8 shows the result of the IL13 phage ELISA. Binding is detected in most conditions, with phage produced in XL-1 blue cells with 1 mM IPTG showing the highest signals. The peptide-Fc-pIX and alternative scaffold molecule-pIX fusions were negative, as expected, and the 6-2 Fab pIX control was positive. The binding was inhibited by adding soluble anti-IL13 antibody, showing that the interaction is specific. To further examine the IL13 binding, an ELISA was set up in which the soluble competition antibody was serially diluted from 50 μg/ml-0.01 μg/ml. A control antibody was also included. FIGS. 9A and B show the effect of soluble antibody competition on IL13 binding of 6-2 IgG pIX and 6-2 Fab pIX, respectively. Inhibition of binding is seen for both constructs, with an IC50 of approximately 0.1 μg/ml. However, for the full IgG pIX construct, the inhibition is incomplete even at very high competitor concentrations, suggesting that some level of un-specific interactions is present.

G. Full IgG pIX Phage Binding to IL13 and IL17

Figure 6:
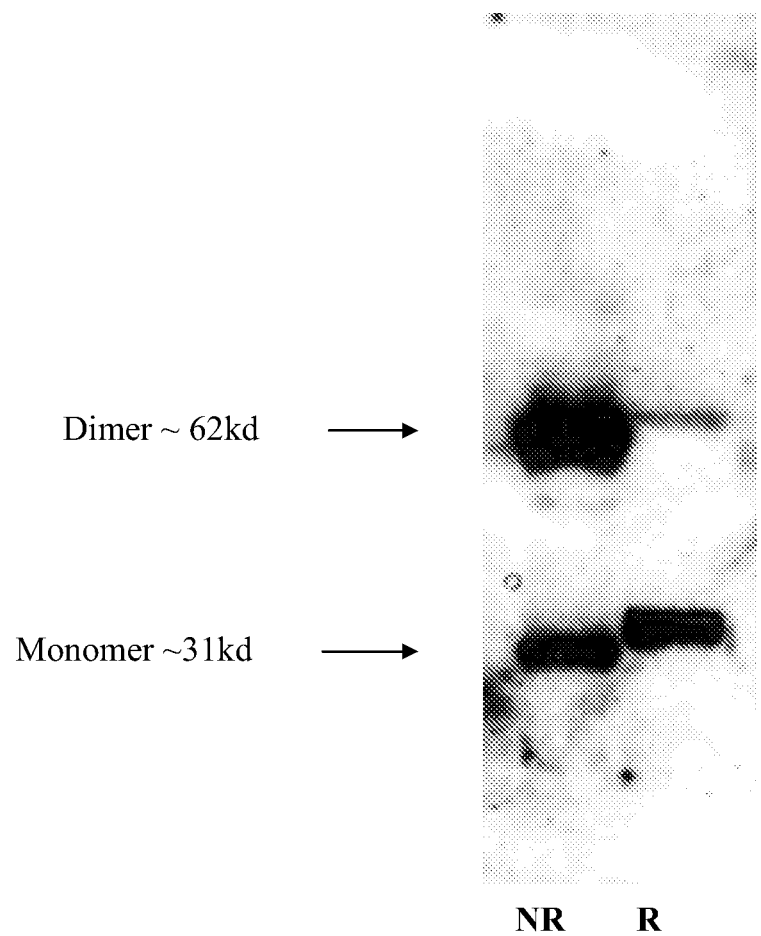
FIG. 6 shows a Western blot using anti-human Fc antibody for detection demonstrating the dimeric nature of the protein isolated and electrophoresed under non-reducing conditions, Lane 1, NR; and reducing conditions, Lane 2, R, showing that under non-reducing the major band is approximately twice the molecular weight as the major band under reducing conditions.
Figure 10:
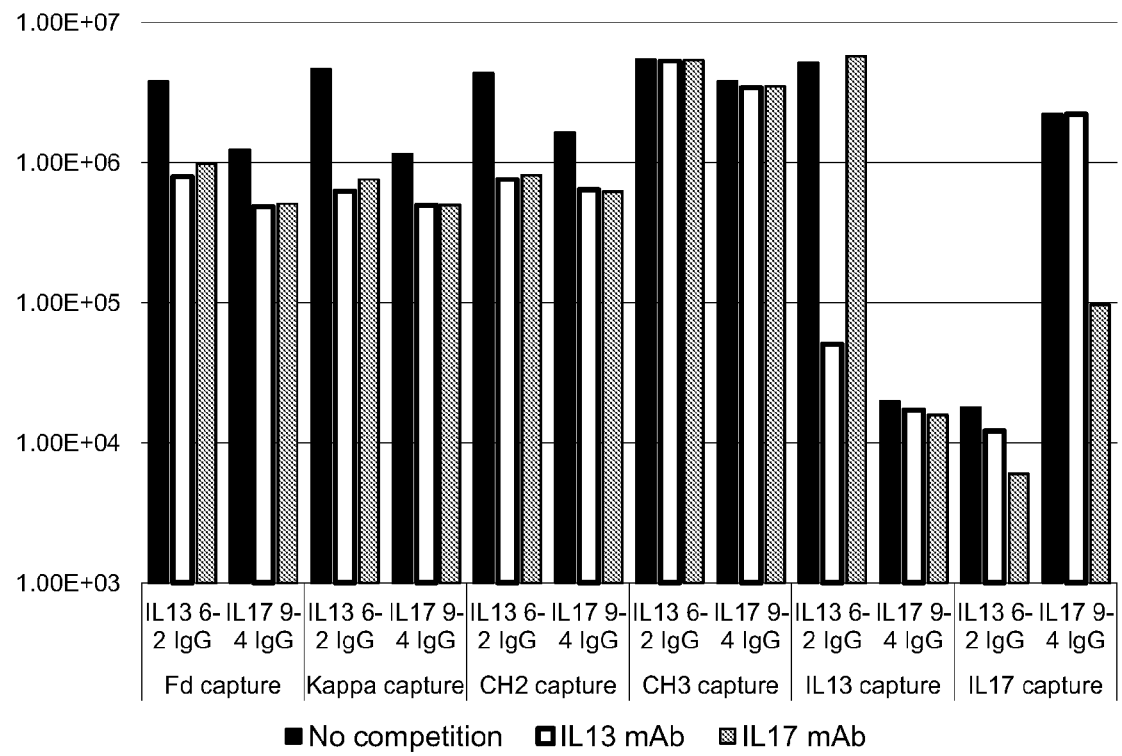
FIG. 10 shows a signal from phage was captured by either of the domain specific antibodies anti-Fd, anti-Kappa, anti-CH2 and anti-CH3 after biotinylated IL13 or IL17A antigens were used to capture phage displaying full IgG constructs of IL13 or IL17A and in the presence or absence of competing soluble anti-IL13 mAb or anti-IL17A mAb. Phage were detected with anti-M13 antibody (y-axis).

A second confirmatory experiment was performed. This was done by cloning a full IgG version of an anti-IL17A antibody. The construct was transformed into XL-1 blue cells and phage was produced as described above. ELISAs were carried out to confirm the display of the IL17 IgG on pIX as well as its binding to human IL17Amut6 antigen as shown in FIG. 6. For each ELISA (Fd capture, kappa capture, CH2 capture, CH3 capture, IL13 capture, and IL17 capture), the phage is either added alone or together with a soluble anti-IL13 mAb or a soluble anti-IL17A mAb. The addition of competitor mAb shows the specificity of the ELISA. As evident in FIG. 10, the IL17 IgG is displayed on pIX, although at lower levels than the IL13 IgG. This is consistent with differences in Fab expression levels between these constructs (data not shown). The specificity of antigen binding can be seen since the anti IL13 IgG on phage does not bind to IL17 and the anti IL17 IgG on phage does not bind to IL13. In addition, the binding of each of the two types of phage can be inhibited by their soluble mAb counterparts.

EXAMPLE 4

Display of Fc-Containing Proteins Fused to pVII

Additionally, we have demonstrated that Fc and MIMETIBODY™ proteins could be displayed on the phage surface using a pVII phagemid system.

What is claimed:

1. A replicable phage vector for the display of a functional, multimeric, interchain disulfide linked protein on the surface of a filamentous phage particle; comprising nucleic acid sequences encoding an inducible promoter and nucleic acid sequences encoding a first polypeptide chain and a second polypeptide chain wherein each chain consists of amino acid residues according to the following formula:

N-(a bacterial secretion signal)-(Formula I)-(a phage coat protein)-C wherein N is the N-terminus and C is the C-terminus;
  wherein the phage coat protein is a phage pIX or pVII protein;
  wherein Formula I is $V1_o$-$Pep_a$-$Flex_n$-$V2_m$-Hinge-$CH_2$—$CH_3$;
  wherein Pep represents a bioactive peptide or polypeptide capable of specifically recognizing a target;
  wherein Flex is an optional flexible linker polypeptide that provides structural flexibility;
  wherein V1 and V2 are bracketing sequences;
  wherein Hinge is at least a portion of an immunoglobulin hinge region selected from the group consisting of: SEQ ID NO: 1-4, SEQ ID NO 1 amino acid residues 11-15, SEQ ID NO 2 amino acid residues 8-12, SEQ ID NO 3 amino acid residues 13-61 and SEQ ID NO 4 amino acid residues 8-12;
  wherein $CH_2$ is at least a portion of an immunoglobulin $CH_2$ constant region;
  wherein $CH_3$ is at least a portion of an immunoglobulin $CH_3$ constant region;
  wherein m, n and o can be zero or can be an integer between 1 and 10, and a can be an integer from 1 to 10;
  wherein said encoded Hinge amino acid sequence comprises at least one cysteine residue;
  wherein a cysteine residue on the first polypeptide chain is capable of becoming oxidatively bonded to a Hinge cysteine residue on the second polypeptide chain; and
  whereby the cysteine bond so formed is an interchain disulfide of the functional multimeric structure being displayed on the surface of the same filamentous phage particle.

2. The phage vector of claim 1 wherein functional activity of the protein structure is selected from protein A binding and FcRn binding.

3. The phage vector of claim 1, wherein the interchain disulfide lies within the amino acid sequence of the antibody hinge domain.

4. The phage vector of claim 3 wherein the $CH_2$ constant region is selected from the group consisting of SEQ ID NOs: 5, 6, 7, and 8 and the $CH_3$ constant region is selected from the group consisting of SEQ ID NOs: 9, 10, 11, and 12.

5. The phage vector of claim 1, wherein the bacterial secretion signal is selected from the group consisting of wild-type pelB sequence SEQ ID NO: 14, wild-type ompA and SEQ ID NO: 15.

6. The phage vector of claim 1, wherein the inducible promoter is a lac promoter or mutant of lac.

7. A phage library of bacterial host cells comprising a nucleic acid phage vector according to claim 3 wherein specific positions within the vector comprises sequences that vary one from another at specific residues.

8. The phage vector of claim 1, wherein the V1 and V2 bracketing sequences are derived from an antibody variable (V) domain Vh framework.

9. The phage vector of claim 8, wherein the V1 is the sequence QIQ and the V2 represents a sequence derived from an immunoglobulin J gene domain and is GTLVTVSS (SEQ ID NO: 13).

* * * * *